United States Patent
Attia et al.

(10) Patent No.: US 9,790,135 B2
(45) Date of Patent: Oct. 17, 2017

(54) USE OF ACYLATED CARBONIC ESTERS OF GLYCEROL IN AGRICULTURE

(71) Applicants: AGRONUTRITION, Carbonne (FR); INSTITUT NATIONAL POLYTECHNIQUE DE TOULOUSE, Toulouse (FR); INSTITUT NATIONAL DE LA RECHERCHE AGRONOMIQUE, Paris (FR)

(72) Inventors: Faouzi Attia, Toulouse (FR); Cedric Cabanes, Pechabou (FR); Monique Guenier, Saint Orens (FR); Zephirin Mouloungui, Toulouse (FR); Bachar Zebib, Toulouse (FR); Romain Valentin, Toulouse (FR); Zaher Abdel Baki, Toulouse (FR)

(73) Assignees: AGRONUTRITION, Carbonne (FR); INSTITUT NATIONAL POLYTECHNIQUE DE TOULOUSE, Toulouse (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 38 days.

(21) Appl. No.: 14/775,165

(22) PCT Filed: Mar. 12, 2014

(86) PCT No.: PCT/FR2014/050567
§ 371 (c)(1),
(2) Date: Sep. 11, 2015

(87) PCT Pub. No.: WO2014/140484
PCT Pub. Date: Sep. 18, 2014

(65) Prior Publication Data
US 2016/0031764 A1 Feb. 4, 2016

(30) Foreign Application Priority Data
Mar. 14, 2013 (FR) ..................... 13 52301

(51) Int. Cl.
*C05G 3/00* (2006.01)
*A01N 25/30* (2006.01)
(Continued)

(52) U.S. Cl.
CPC ............... *C05G 3/00* (2013.01); *A01N 25/30* (2013.01); *A01N 43/28* (2013.01); *A01N 43/32* (2013.01);
(Continued)

(58) Field of Classification Search
CPC . C05G 3/00; C05G 3/02; A01N 25/30; A01N 43/28; A01N 43/32; A01N 47/06;
(Continued)

(56) References Cited

U.S. PATENT DOCUMENTS 4,882,391 A * 11/1989 Brindopke ................ C08F 8/32
525/327.2
6,716,443 B1 4/2004 Abribat et al.
(Continued)

FOREIGN PATENT DOCUMENTS

EP 1 366 663 A1 12/2003
FR 2 874 217 A1 2/2006
(Continued)

OTHER PUBLICATIONS

Mouloungui et al. (2001), Eur. J. Lipid Sci. Technol., 103, 216-222 "Study of the acyl transfer reaction : Structure and properties of glycerol esters" cited in Specification.
(Continued)

*Primary Examiner* — Jennifer A Smith
(74) *Attorney, Agent, or Firm* — Young & Thompson

(57) ABSTRACT

A process for treating plants, including the application of at least one compound, termed carbonic ester of glycerol,
(Continued)

including at least one carboxylic ester function formed by a carbonic acid-derived group and at least one glycerol-derived group, with the exception of cyclic glyceryl carbonate including five ring members.

10 Claims, 4 Drawing Sheets

(51) Int. Cl.
A01N 43/28 (2006.01)
A01N 43/32 (2006.01)
A01N 47/06 (2006.01)
C05G 3/02 (2006.01)
C05D 9/02 (2006.01)
C05F 11/08 (2006.01)
C07C 69/96 (2006.01)
C07D 317/36 (2006.01)
C07D 319/06 (2006.01)

(52) U.S. Cl.
CPC ............... A01N 47/06 (2013.01); C05D 9/02 (2013.01); C05F 11/08 (2013.01); C05G 3/02 (2013.01); C07C 69/96 (2013.01); C07D 317/36 (2013.01); C07D 319/06 (2013.01)

(58) Field of Classification Search
CPC ........... C05D 9/02; C05F 11/08; C07C 69/96; C07D 317/36; C07D 319/06
See application file for complete search history.

(56) References Cited

U.S. PATENT DOCUMENTS

2004/0030176 A1* 2/2004 Ohrbom ................ C07C 217/12
560/158
2009/0036642 A1 2/2009 Truong Dinh et al.
2009/0054271 A1 2/2009 Dinh et al.

FOREIGN PATENT DOCUMENTS

| | | | |
|---|---|---|---|
| FR | 2 880 025 A1 | 6/2006 | |
| JP | 2006/182684 A | 7/2006 | |
| JP | 2006182684 A * | 7/2006 | |
| JP | WO 2013042677 A1 * | 3/2013 | ............ C09J 167/04 |
| WO | 00/51427 A1 | 9/2000 | |

OTHER PUBLICATIONS

International Search Report, dated Jun. 23, 2014, from corresponding PCT application.

* cited by examiner

USE OF ACYLATED CARBONIC ESTERS OF GLYCEROL IN AGRICULTURE

The invention relates to new uses of glycerol carbonic esters.

Glycerol carbonic esters are known for their ability to be used as additives in industrial lubricants—especially lubricants for motor vehicles—and as additives in oil-drilling muds.

In particular, there are known from Mouloungui et al. (2001), Eur. J. Lipid Sci. Technol., 103, 216-222 "*Study of the acyl transfer reaction: Structure and properties of glycerol esters*" the properties of heat stability and oxidation resistance of cyclic glycerol carbonate acetate, of cyclic glycerol carbonate butyrate, of cyclic glycerol carbonate octanoate, of cyclic glycerol carbonate dodecanoate, of cyclic glycerol carbonate palmitate, of cyclic glycerol carbonate stearate and of cyclic glycerol carbonate oleate and their applications as lubricants and/or additives of a lubricant composition.

Uses of cyclic glycerol carbonate in agriculture are known from JP2006182684, EP1366663 and WO 00/51427.

The invention aims to propose novel uses of cyclic α/α'-acylated glycerol carbonic esters and, more generally, to propose novel uses of glycerol carbonic esters.

To that end, the invention relates to a method for the treatment of plants, comprising the application of at least one compound, named glycerol carbonic ester, comprising at least one carboxylic ester function formed by a group derived from carbonic acid and at least one group derived from glycerol, with the exception of the cyclic glycerol carbonate having five ring members. The invention relates to a method for the treatment of plants which comprises the application of at least one such glycerol carbonic ester to a plant.

Cyclic glycerol carbonate having five ring members is understood as being the glycerol carbonic ester of the following formula (VI):

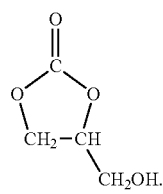
(VI)

Accordingly, the invention relates to the use, as an input in agriculture, of at least one compound, named glycerol carbonic ester, comprising at least one carboxylic ester function formed by a group derived from carbonic acid and at least one group derived from glycerol, with the exception of the cyclic glycerol carbonate having five ring members. More particularly, the invention relates to the use, as an agricultural input, of such glycerol carbonic ester(s) applied to plants.

Throughout the text:

group "derived from glycerol" denotes any group of the following formula:

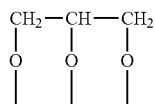

wherein at least one hydrogen atom of the hydroxyl groups of the glycerol is substituted by an organic group other than hydrogen; and group "derived from carbonic acid" denotes any group of the following formula:

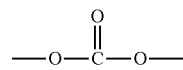

wherein at least one hydrogen atom of the carbonic acid is substituted by an organic group other than hydrogen.

Advantageously and according to the invention, at least one glycerol carbonic ester is chosen from the group formed of linear glycerol carbonic esters and cyclic glycerol carbonic esters.

A glycerol carbonic ester can be chosen from the group formed of linear glycerol carbonic esters having at least one group of atoms of the following general formula (I):

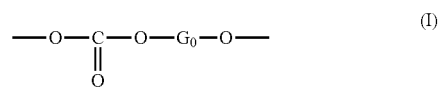
(I)

wherein $G_0$ is chosen from the group formed of:

α/α'-acylated propylene groups of the following general formula (II):

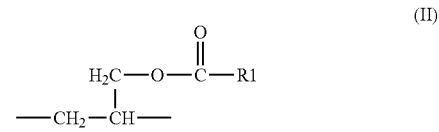
(II)

β-acylated propylene groups of the following general formula (III):

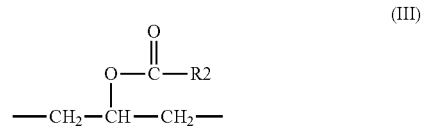
(III)

the α/α'-hydroxylated propylene group of the following formula (IV):

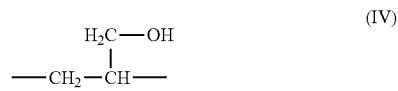
(IV)

the β-hydroxylated propylene group of the following formula (V):

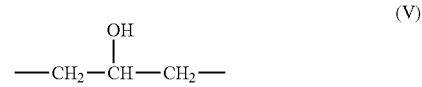
(V)

R1 and R2 being organic groups formed of elements chosen from the group formed of carbon (C), hydrogen (H) and oxygen (O).

A glycerol carbonic ester can be chosen from the group formed of linear glycerol carbonic esters having at least one group of atoms of the following general formula (I'):

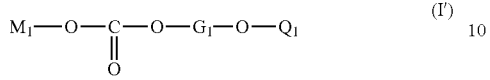

wherein:
G$_1$ is chosen from the group formed of:
α/α'-acylated propylene groups of the general formula (II);
β-acylated propylene groups of the general formula (III);
the α/α'-hydroxylated propylene group of formula (IV);
the β-hydroxylated propylene group of formula (V);
Q$_1$ is chosen from the group formed of hydrogen (H) and organic groups formed of at least two atoms bonded by covalent bonds, said atoms belonging to the group formed of carbon (C), hydrogen (H) and oxygen (O); and
M$_1$ represents an organic group formed of at least two atoms bonded by covalent bonds, said atoms belonging to the group formed of carbon (C), hydrogen (H) and oxygen (O).

A glycerol carbonic ester can be a cyclic α/α'-acylated glycerol carbonic ester of the following general formula (VIII):

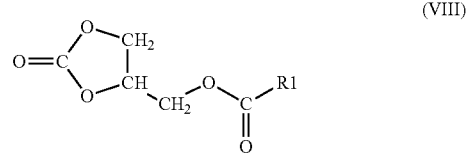

wherein R1 is an organic group of elements chosen from the group formed of carbon (C), hydrogen (H) and oxygen (O).

A glycerol carbonic ester can be a cyclic β-acylated glycerol carbonic ester of the following general formula (IX):

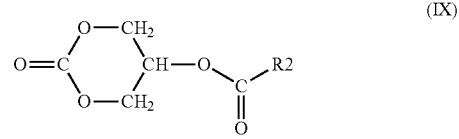

wherein R2 is an organic group formed of elements chosen from the group formed of carbon (C), hydrogen (H) and oxygen (O). A glycerol carbonic ester can be a cyclic β-acylated glycerol carbonic ester having six ring members.

A glycerol carbonic ester can be chosen from the group formed of linear acylated glycerol carbonic esters—especially linear glycerol carbonic oligomers—of the following general formula (X):

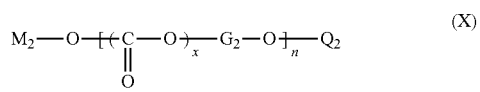

wherein:
x is an integer equal to 0 or to 1 which can vary in formula (X) according to each group of formula (X-a):

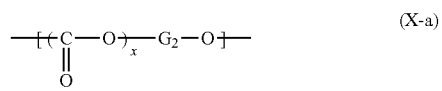

x not always being zero;
n is an integer from 1 to 20—especially from 1 to 10—inclusive;
Q$_2$ is chosen from the group formed of hydrogen (H) and organic groups formed of at least two atoms bonded by covalent bonds, said atoms belonging to the group formed of carbon (C), hydrogen (H) and oxygen (O); and
M$_2$ represents an organic group formed of at least two atoms bonded by covalent bonds, said atoms belonging to the group formed of carbon (C), hydrogen (H) and oxygen (O); and
G$_2$ represents a group of atoms chosen from the group formed of:
α/α'-acylated propyl groups of the general formula (II), and
β-acylated propyl groups of the general formula (III).

The glycerol carbonic ester of formula (I), (I') or (X) has a molar mass greater than 400 g/mol. Advantageously, the linear α/α'-acylated glycerol carbonic ester of the general formula (X) has a molar mass greater than 400 g/mol.

The groups R1 and R2 of glycerol carbonic esters can be aliphatic hydrocarbon groups having from 1 to 25 carbon atoms. Advantageously, R1 and R2 are chosen independently of one another. R1 and R2 can therefore be identical or different.

In particular, the groups R1 and R2 can be chosen from the group formed of methyl (—CH$_3$), ethyl (—CH$_2$—CH$_3$), n-propyl (—CH$_2$—CH$_2$—CH$_3$), iso-propyl (—CH(CH$_3$)$_2$), n-butyl (—CH$_2$—CH$_2$—CH$_2$—CH$_3$), iso-butyl (—CH$_2$—CH(CH$_3$)$_2$), tert-butyl (—C(CH$_3$)$_3$), n-pentyl (—(CH$_2$)$_4$—CH$_3$), n-hexyl (—(CH$_2$)$_5$—CH$_3$), n-heptyl (—(CH$_2$)$_6$—CH$_3$), n-octyl (—(CH$_2$)$_7$—CH$_3$), n-nonyl (—(CH$_2$)$_8$—CH$_3$), n-decyl (—(CH$_2$)$_9$—CH$_3$), n-undecyl (—(CH$_2$)$_{10}$—CH$_3$), n-dodecyl (—(CH$_2$)$_{11}$—CH$_3$), n-tridecyl (—(CH$_2$)$_{12}$—CH$_3$), n-tetradecyl (—(CH$_2$)$_{13}$—CH$_3$), n-pentadecyl (—(CH$_2$)$_{14}$—CH$_3$), n-hexadecyl (—(CH$_2$)$_{15}$—CH$_3$), n-heptadecyl (—(CH$_2$)$_{16}$—CH$_3$), n-octadecyl (—(CH$_2$)$_{17}$—CH$_3$), n-nonadecyl (—(CH$_2$)$_{18}$—CH$_3$), n-dodecadecyl (—(CH$_2$)$_{19}$—CH$_3$).

The groups R1 and R2 can also be chosen from the group formed of unsaturated alkyls—especially a 9-ene-decyl group (—CH═CH—(CH$_2$)$_7$—CH$_3$) and a 9-ene-heptadecyl group (—(CH$_2$)$_7$—CH═CH—(CH$_2$)$_7$—CH$_3$).

Such cyclic α/α'-acylated or β-acylated glycerol carbonic esters are multifunctional compounds in that they are both solvent compounds and compounds.

Accordingly, the invention relates to a method for the treatment of plants comprising the application of a treatment composition comprising at least one glycerol carbonic ester—especially at least one glycerol carbonate ester according to at least one of formulae (I), (I'), (VIII), (IX) or (X)—in contact with said plants.

The inventors have found that the glycerol carbonic esters, when they are brought into contact with plants—especially but not exclusively with the parts of plants above the soil—on the one hand do not impair the growth and development of the plants and on the other hand even have numerous advantages as agricultural inputs. In particular they do not damage the cuticle of the leaves of the plants and do not cause burning of the plants when they are applied to the parts of plants above the soil.

The glycerol carbonic esters are suitable for application to plants and comply with environmental protection and conservation standards. They are not in themselves toxic to human or animal health. They are biodegradable, they do not present any risk of accumulating in the soil and of contaminating or damaging the environment when they are applied to plants and/or introduced into the soil—for example by being washed in by rainwater or by watering—and by runoff. The glycerol carbonic esters can be "biosourced", that is to say obtained from inexpensive and renewable natural resources—especially from plant resources. They therefore have a low cost price and can be applied economically in the open field to plants. Furthermore, they have properties of supplementing and improving the efficiency of active substances. As such, they can allow the doses of such active substances which are to be applied to plant crops and in the environment to be reduced and contribute to the conservation of that environment.

In an embodiment of a method for the treatment of plants according to the invention there is applied to plants a treatment composition comprising at least one glycerol carbonic ester and optionally a "phyto-acceptable" excipient, that is to say an excipient which is compatible with its application to plants and is acceptable to plants. Advantageously and according to the invention, at least one glycerol carbonic ester—especially such a treatment composition—is applied in contact with plants at any stage of their development or of their growth. At least one glycerol carbonic ester—especially such a treatment composition—can be applied to plants at the stage of seeds, or to plants at the stage of plantlets, that is to say to a young plant that has only a limited number of leaves, or to juvenile plants—especially to plants at a stage preceding flowering—or to plants during flowering (before, during or after pollination), or to plants after fertilization, or to plants during fruiting. It is also possible to apply at least one glycerol carbonic ester—especially such a treatment composition—in the plant cultivation substrate—for example in the soil—so as to permit contact of at least one glycerol carbonic ester—especially of such a treatment composition—with the underground parts—especially, for example, the roots, the rhizomes, the tubers—of the plants. It is also possible to apply at least one glycerol carbonic ester—especially such a treatment composition—in a nutritive medium suitable for addition to the plant cultivation substrate.

Advantageously and according to the invention, at least one glycerol carbonic ester is applied in contact with underground parts of plants.

Advantageously and according to the invention, at least one glycerol carbonic ester—especially such a treatment composition—is applied in contact with parts of plants in cultivation that are above the soil. In particular, at least one glycerol carbonic ester—especially such a treatment composition—is applied to the flowers, the fruits, the leaves, the stems of plants in cultivation.

It is possible in particular to apply at least one glycerol carbonic ester—especially such a treatment composition—to plants in cultivation in the open field or to plants in cultivation in a greenhouse or to plants in soilless cultivation.

Advantageously and according to the invention, at least one glycerol carbonic ester—especially such a treatment composition—is applied to a market-gardening crop, to an industrial crop or to a field crop.

Advantageously and according to the invention, at least one glycerol carbonic ester—especially such a treatment composition—is applied in contact with a plant chosen from the group formed of fruit trees—especially olive trees, apricot trees, cherry trees, quince trees, almond trees, fig trees, hazel trees, walnut trees, peach trees, pear trees, apple trees, plum trees, vines and citrus fruit trees—ornamental trees and shrubs, vegetable plants—especially asparagus, aubergines, Swiss chard, beetroot, carrots, celery, chicory, endives, crucifers or brassicas (for example cabbages), cucumbers, gherkins, courgettes, shallots, onions, broad beans, spring beans, winter beans, strawberry plants, raspberry plants, haricot beans, lettuce, curly endives, escaroles, hops, lentils, alfalfa, lamb's lettuce, maize, melons, turnips, leeks, peas, peppers, potatoes, radish, swede, soya, tobacco, tomatoes, sunflowers—, cereals—especially wheat, rape, flax, seed flax, fibre flax, barley, sorghum—, various floral crops—especially chrysanthemums, hortensias, carnations, roses, tulips—and aromatic plants—especially parsley, garlic, chives.

The glycerol carbonic esters can, surprisingly, contribute in particular to improving the effectiveness of a plant treatment composition. Advantageously and according to the invention, at least one glycerol carbonic ester is thus used as an adjuvant for vectorizing at least one active agent for plant treatment other than a glycerol carbonic ester, especially an active agent chosen from the group formed of agents that act upon the germination of seeds, growth control agents, plant development agents, agents for stimulating photosynthesis, and nutriments for plants.

Advantageously and according to the invention, at least one glycerol carbonic ester is applied in association with at least one active agent, other than a glycerol carbonic ester, chosen from the group formed of agents that act upon the germination of seeds, growth control agents, plant development agents, agents for stimulating photosynthesis, and nutriments for plants.

The glycerol carbonic esters can, surprisingly, contribute in particular to improving the effectiveness of a plant nutritive composition. Advantageously and according to the invention, at least one glycerol carbonic ester is thus used as an adjuvant for vectorizing at least one nutritive element for plants. The invention accordingly relates in particular to a method for the treatment of plants comprising the application of at least one glycerol carbonic ester in association with at least one plant nutritive agent.

The application of at least one glycerol carbonic ester can be carried out separately from the application of at least one other such active (especially nutritive) agent—in particular with distinct treatment compositions applied simultaneously or, on the contrary, in succession. Advantageously and according to the invention, the application of at least one glycerol carbonic ester can be carried out at the same time as the application of at least one other such active (in particular nutritive) agent—in particular by application of the same treatment, especially nutritive, composition. Advantageously and according to the invention, at least one glycerol carbonic ester is used in a treatment, especially nutritive, composition which is to be applied to plants and further comprises at least one other plant treatment, especially nutritive, agent. In a treatment, especially nutritive, composition according to the invention, at least one glycerol carbonic ester can serve as a phyto-acceptable excipient. In a variant according to the invention, said treatment, especially nutritive, composition further comprises a phyto-acceptable excipient other than a glycerol carbonic ester.

1. Treatment of Seeds

A first aspect of the invention relates to the use of at least one glycerol carbonic ester—especially of a treatment composition comprising at least one glycerol carbonic ester—for the treatment of seeds of at least one plant. The invention therefore relates to a method for the treatment of seeds of at least one plant, wherein the seeds are brought into contact with at least one glycerol carbonic ester—especially with a seed treatment composition comprising at least one glycerol carbonic ester.

Advantageously and according to the invention, at least one glycerol carbonic ester—especially at least one glycerol carbonic ester of formula (I), (I'), (VIII), (IX) or (X)—is applied in contact with plant seeds. A seed treatment composition comprising at least one glycerol carbonic ester is applied to plant seeds.

A method for the treatment of seeds according to the invention can be suitable for protecting the seeds from germination before they are buried in the soil and/or for activating germination of the seeds after they have been buried in the soil.

Advantageously, in a first variant of this first aspect of the invention, the seeds are coated with a seed treatment composition comprising at least one glycerol carbonic ester and at least one microorganism chosen from the group formed of mycorrhizal fungi, rhizobacteria (for example *Azotobacter, Azospirillum, Pseudomonas*). In particular, the glycerol carbonic ester allows the microorganisms to adhere to the seeds and the microorganisms to develop during germination of the seeds.

In particular, such a microorganism can be a microorganism known by the name PGPR (plant growth promoting rhizobacteria) and including bacteria of the rhizosphere which are beneficial to the growth and health of plants.

A seed treatment composition according to the invention can comprise a proportion by mass of at least one glycerol carbonic ester of less than 50%, in particular less than 10%, preferably from 0.1% to 5%.

In a second variant of this first aspect of the invention, a seed treatment composition—especially a seed treatment composition comprising at least one glycerol carbonic ester and at least one microorganism chosen from the group formed of mycorrhizal fungi and rhizobacteria—is applied to the seeds during sowing, that is to say at the same time as sowing, or after sowing.

According to a third variant, there is applied to seeds of at least one plant a treatment composition comprising at least one glycerol carbonic ester and at least one agent that stimulates the germination of the seeds other than a glycerol carbonic ester.

The invention relates also to a plant seed treatment composition comprising at least one glycerol carbonic ester—especially at least one glycerol carbonic ester of formula (I), (I'), (VIII), (IX) or (X)—and at least one substance that acts upon the germination of seeds—especially at least one microorganism—other than a glycerol carbonic ester. A plant seed treatment composition according to the invention can also further comprise a phyto-acceptable excipient other than a glycerol carbonic ester.

A method for the treatment of plant seeds and a plant treatment composition according to the invention especially allow:
- the germination of the seeds and the growth of the plants from those seeds to be stimulated,
- the resistance of the plants obtained from those seeds to phyto-pathogenic organisms to be increased,
- the rooting of the plants to be improved,
- the assimilation and fixing of nutritive elements, especially chosen from nitrogen (N), phosphorus (P), potassium (K) and iron (Fe) and the oligoelements, to be promoted,
- the fixing of atmospheric nitrogen to be promoted,
- the formation of a symbiosis between said microorganism and the plants obtained from those seeds to be promoted; and
- generally, the production yield of the plants to be increased.

The invention relates also to a plant seed treatment composition comprising at least one glycerol carbonic ester and, where appropriate, at least one microorganism chosen from the group formed of mycorrhizal fungi and rhizobacteria and/or at least one substance that acts upon—especially stimulates—the germination of seed(s), other than a glycerol carbonic ester. A plant seed treatment composition can also optionally comprise a phyto-acceptable excipient other than a glycerol carbonic ester.

2. Photosynthesis Stimulation Treatment

Another aspect of the invention relates to the use of at least one glycerol carbonic ester—especially at least one glycerol carbonic ester of formula (I), (I'), (VIII), (IX) or (X)—for stimulating the photosynthesis of plants. The invention therefore relates to a treatment method for stimulating the photosynthesis of plants, comprising the application of at least one glycerol carbonic ester—especially of a composition for stimulating photosynthesis comprising at least one glycerol carbonic ester. This aspect of the invention relates also to the use of a composition for stimulating photosynthesis which comprises at least one glycerol carbonic ester—especially at least one glycerol carbonic ester of formula (I), (I'), (VIII), (IX) or (X)—and at least one agent that acts upon the stimulation of photosynthesis, other than a glycerol carbonic ester. The invention therefore relates to a method for stimulating the photosynthesis of plants, wherein there is applied at least one glycerol carbonic ester—especially a composition for stimulating photosynthesis comprising such a glycerol carbonic ester. This aspect of the invention therefore relates also to a composition for stimulating photosynthesis comprising at least one carbonic acid ester of glycerol—especially at least one glycerol carbonic ester of formula (I), (I'), (VIII), (IX) or (X)—and at least one agent that acts upon the stimulation of photosynthesis, other than a glycerol carbonic ester, and, optionally, a phyto-acceptable excipient other than a glycerol carbonic ester.

3. Nutritive Treatment/Fertilization

Another aspect of the invention relates to the use of at least one glycerol carbonic ester—especially at least one glycerol carbonic ester of formula (I), (I'), (VIII), (IX) or (X)—in a nutritive treatment, in particular for controlling the growth and/or the development of plants, especially by fertilization and/or by application to the plants.

Accordingly, the invention relates to a nutritive treatment method for plants. The invention relates in particular to a nutritive treatment method for plants which comprises applying at least one glycerol carbonic ester—especially a nutritive composition. According to the invention, a nutritive composition is applied to plants in any of their stages of growth and/or development.

Advantageously and according to the invention, there is applied in contact with plants a nutritive composition comprising at least one glycerol carbonic ester and at least one solid in the divided state comprising at least one compound chosen from the group formed of nutritive elements of plants.

Advantageously, a nutritive composition comprising at least one glycerol carbonic ester and at least one nutritive treatment agent for plants other than a glycerol carbonic ester is applied.

The invention extends to a nutritive composition comprising at least one glycerol carbonic ester—especially at least one glycerol carbonic ester of formula (I), (I'), (VIII), (IX) or (X)—and at least one nutritive agent of plants other than a glycerol carbonic ester and, optionally, a phyto-acceptable excipient other than a glycerol carbonic ester. A nutritive composition according to the invention can be in any form appropriate to its administration in contact with plants and/or their substrate, especially in the form of granules, powder, liquid solution or suspension for spreading or spraying, or the like.

The invention relates in particular to the use of at least one glycerol carbonic ester—especially of a nutritive composition comprising at least one glycerol carbonic ester—for the nutritive treatment of plants by direct application to parts of the plants above the soil and/or to underground parts of the plants. Advantageously, a nutritive composition comprising at least one glycerol carbonic ester and at least one nutritive element of plants other than a glycerol carbonic ester is applied. The nutritive composition according to the invention is advantageously chosen to be able to permit the release of at least one nutritive element through the cuticle of plants. Advantageously and according to the invention, the nutritive composition is applied to at least a part of the plants that is above the soil—especially to at least a part of the foliage of the plants. A nutritive composition according to the invention is suitable in particular for application to the parts of the plants that are above the soil. For example, a liquid nutritive composition is applied by fogging (by means of an atomizer). In particular, the nutritive composition according to the invention can be applied especially to vegetable plants or to ornamental plants in cultivation. The nutritive composition according to the invention can thus be used especially in horticulture.

The inventors have observed that a nutritive composition comprising at least one glycerol carbonic ester surprisingly improves the assimilation of nutritive elements by the plant. Without being bound by this possible explanation, this assimilation may arise owing to the fact that a glycerol carbonic ester allows the interactions of droplets of the nutritive composition that are formed on the surface of parts above the soil—especially on the surface of the leaves—of plants to be controlled. Such a nutritive composition appears to reduce the value of the contact angle formed on the surface of vine leaves, on the surface of soya leaves and on the surface of rape leaves, in comparison with a nutritive composition without glycerol carbonic ester.

Advantageously and according to a variant, the invention relates to a fertilization method in which at least one glycerol carbonic ester is applied as a conditioner for the cultivation substrate—for example the soil. Advantageously and according to the invention there is applied a fertilizing nutritive composition which is chosen to promote the assimilation of mineral elements by the roots and to improve the growth and the root development of the plants. It is also possible, for example, to use such a fertilizing nutritive composition on plants during the taking of cuttings therefrom or during repotting of the plants.

The invention extends in particular to a fertilizing nutritive composition comprising at least one glycerol carbonic ester—especially at least one glycerol carbonic ester of formula (I), (I'), (VIII), (IX) or (X)—and at least one microorganism chosen from the group formed of mycorrhizal fungi and rhizobacteria. A fertilizing nutritive composition according to the invention can also optionally comprise a phyto-acceptable excipient other than a glycerol carbonic ester.

Such a nutritive treatment (by direct application and/or fertilization) of plants allows the nutritive elements necessary for their development and for their growth to be supplied to said plants, with a view to obtaining an optimum production yield—given the quality of the soil, the climate, the genetic potential of said plants and the supply of water—and optimum nutritional and organoleptic qualities.

Advantageously there is applied a nutritive composition comprising at least one glycerol carbonic ester and at least one nutritive element—especially at least one mineral nutritive element useful in the development and/or the growth of the plants.

Advantageously there is applied a nutritive composition according to the invention comprising at least one glycerol carbonic ester in a dosage chosen to satisfy the nutritional requirements of the plants. In particular, a nutritive composition according to the invention is applied to plants in order to compensate for a nutritional deficiency of said plants in terms of macroelements (for example nitrogen, phosphorus, potassium), in terms of meso-elements (for example calcium, sulfur, magnesium) or in terms of oligoelements (for example manganese, copper, iron, boron, molybdenum, zinc, nickel, selenium, silicon or sodium).

Advantageously, it is possible to apply a nutritive composition according to the invention to a plant having a deficiency of at least one nutritive element in order to compensate for that deficiency. In this case, at least one glycerol carbonic ester is advantageously applied in association with at least one nutritive agent chosen to compensate for said deficiency.

It is possible to apply the nutritive composition according to the invention in any possible form, for example in the form of a powder, in the form of granules—especially in the form of microgranules—, in the form of a liquid solution or in the form of a concentrated suspension of said nutritive agent, or the like.

In one embodiment of the invention, there is first prepared a concentrated colloidal suspension of at least one solid in the divided state comprising at least one nutritive element of plants in a liquid phase comprising at least one glycerol carbonic ester, and then said concentrated colloidal suspension is diluted in water to form a nutritive composition for application for the treatment of plants.

Advantageously there is prepared a concentrated colloidal suspension comprising at least one glycerol carbonic ester, glycerol, water and a solid in the divided state comprising at least one nutritive element of plants chosen from the group formed of nitrogen (N), phosphorus (P), potassium (K), calcium (Ca), magnesium (Mg), sulfur (S), iron (Fe), copper (Cu), sodium (Na), zinc (Zn), boron (B), molybdenum (Mo), silicon (Si), selenium (Se) and nickel (Ni), for example manganese carbonate ($MnCO_3$) and/or manganese sulfate ($MnSO_4$), and said concentrated colloidal suspension is diluted in an aqueous phase to form the nutritive composition. By way of example, from 1 to 2 volume(s) of concentrated colloidal suspension are diluted in 100 volumes of water to form the nutritive composition.

The invention relates also to a concentrated colloidal suspension and a nutritive composition comprising at least one glycerol carbonic ester and at least one solid in the divided state comprising at least one nutritive element of plants chosen from the group formed of nitrogen (N), phosphorus (P), potassium (K), calcium (Ca), magnesium (Mg), sulfur (S), iron (Fe), copper (Cu), sodium (Na), zinc (Zn), boron (B), molybdenum (Mo), silicon (Si), selenium (Se) and nickel (Ni). In particular, the concentrated colloidal suspension comprises at least one nutritive element of plants. In particular, the concentrated colloidal suspension comprises at least one nutritive element chosen from the group formed of manganese carbonate ($MnCO_3$), manganese sulfate ($MnSO_4$), magnesium hydroxide ($Mg(OH)_2$), zinc oxide (ZnO), calcium oxide (CaO), iron chelate—especially chelate of EDTA or chelate of EDDHA (ethylenediamine-N,N'-bis-(2-hydroxyphenylacetic acid) and iron—, copper chelate—especially chelate of EDTA and copper—, zinc chelate—especially chelate of EDTA and zinc—, iron sulfate, copper sulfate, zinc sulfate and phosphorus pentoxide ($P_2O_5$).

The concentrated colloidal suspension has a concentration of the solid in the divided state of from 0.001 g/l to 2 kg/l. In particular, the concentrated colloidal suspension of manganese carbonate ($MnCO_3$) has a concentration of manganese of from 80 g/l to 600 g/l.

The concentrated colloidal suspension is stable towards sedimentation over time—in particular over a period of 12 months—and is capable of being stored at a temperature of from −50° C. to +50° C. without any alteration of its rheological properties or of the stimulating and/or nutritive properties of the nutritive composition obtained by dilution of the concentrated colloidal suspension. Such a concentrated colloidal suspension can therefore be proposed for sale, marketed and distributed while retaining the stimulating and/or nutritive properties of the nutritive composition.

Advantageously, the concentrated colloidal suspension comprises from 1% to 5% glycerol carbonic ester, from 1% to 20% water, from 15% to 50% glycerol and from 10% to 90% of the solid in the divided state comprising at least one nutritive element of plants—especially manganese carbonate ($MnCO_3$) and/or manganese sulfate ($MnSO_4$)—, the percentages representing proportions by mass.

Advantageously and according to the invention, the concentrated colloidal suspension and the nutritive composition can comprise a plurality of glycerol carbonic esters and/or a plurality of nutritive elements of plants.

Advantageously and according to the invention, the concentrated colloidal suspension and the nutritive composition comprise at least one glycerol carbonic ester and at least one solid in the divided state comprising at least one compound chosen from the group formed of the nutritive elements of plants, for example manganese carbonate ($MnCO_3$) and/or manganese sulfate ($MnSO_4$).

Advantageously, at least one solid in the divided state is formed of solid particles having a mean size of from 1.5 μm to 2.5 μm, especially of approximately 2 μm.

Advantageously, at least one solid in the divided state is chosen from the group formed of materials which are substantially insoluble in water and in glycerol carbonic esters.

Advantageously and according to the invention, the concentrated colloidal suspension and the nutritive composition comprise as the glycerol carbonic ester at least one linear α/α'-acylated glycerol carbonic ester of formula (I), (I') or (X).

Advantageously and according to the invention, the concentrated colloidal suspension and the nutritive composition comprise as the glycerol carbonic ester at least one glycerol carbonic ester of formula (I), (I'), (VIII), (IX) or (X).

Advantageously, at least one glycerol carbonic ester of the concentrated colloidal suspension and of the nutritive composition is chosen from the group formed of:
  the cyclic glycerol carbonate having six ring members;
  the cyclic α/α'-acylated glycerol carbonic ester of formula (VIII) wherein R1 is a methyl group;
  the cyclic α/α'-acylated glycerol carbonic ester of formula (VIII) wherein R1 is an n-hexyl group;
  the cyclic α/α'-acylated glycerol carbonic ester of formula (VIII) wherein R1 is an n-octyl group;
  the cyclic α/α'-acylated glycerol carbonic ester of formula (VIII) wherein R1 is a 9-ene-decyl group;
  the cyclic α/α'-acylated glycerol carbonic ester of formula (VIII) wherein R1 is an oleyl group;
  cyclic β-acylated glycerol carbonic esters of formula (IX);
  linear glycerol carbonic esters of formula (X).

A colloidal suspension according to the invention can optionally comprise a phyto-acceptable excipient other than a glycerol carbonic ester.

Advantageously and according to the invention, the concentrated colloidal suspension and the nutritive composition also comprise at least one fat chosen from the group formed of jojoba oil (in a proportion of from 0.1% to 5%—especially of approximately 1%), triglycerides—especially oleic triglycerides—(in a proportion of from 0.1% to 5%), and oleic acid salts (in a proportion of from 0.5% to 5%).

Jojoba oil is extracted from seeds of *Simmondsia chinensis* in the form of a composition of esters of substantially unsaturated fatty acids (especially eicosenoic acid, docosenoic acid and oleic acid) and fatty alcohol, each ester having from 36 to 46 carbon atoms.

Advantageously, it is possible for the concentrated colloidal suspension and/or the nutritive composition also to comprise at least one mineral or organic compound chosen from the group formed of dispersing agents, emulsifiers, stabilizers and gelling agents.

Advantageously and according to the invention, the concentrated colloidal suspension and the nutritive composition according to the invention comprise:
  at least one glycerol carbonic ester;
  glycerol;
  at least one compound chosen from the group formed of zinc sulfate ($ZnSO_4$), zinc stearate ($Zn(C_{18}H_{35}O_2)_2$), iron sulfate ($FeSO_4$), ferric phosphate ($FePO_4$), manganese sulfate ($MnSO_4$), zinc oxide (ZnO), calcium carbonate ($Ca_2CO_3$), sodium carbonate ($Na_2CO_3$) and sodium sulfate ($Na_2SO_4$); and
  at least one solid in the divided state comprising at least one compound chosen from the group formed of nutritive elements of plants, especially manganese carbonate ($MnCO_3$) and/or manganese sulfate ($MnSO_4$).

The invention relates in particular to vectorization adjuvants for nutritive compositions of plants. Such an adjuvant not only allows particles of solid material in the divided state to be maintained in suspension in a concentrated colloidal suspension and in the nutritive composition, but also permits controlled release of the nutritive elements, for example rapid release of nutritive element(s) for a period of from one to four days following application, or sustained release—especially delayed release—of nutritive element(s), depending on the chosen glycerol carbonic esters. Such an adjuvant in the form of a concentrated colloidal suspension has a viscosity which can be adjusted, and also allows the viscosity of the nutritive composition to be adjusted. Such an adjuvant is also thixotropic. It can be stored at low temperature without freezing. Such an adjuvant is miscible with water and can be diluted in water extemporaneously prior to application to plants.

The invention extends also to a plant treatment composition comprising at least one glycerol carbonic ester—especially at least one glycerol carbonic ester of formula (I), (I'), (VIII), (IX) or (X)—and at least one active agent, other than a glycerol carbonic ester, chosen from the group formed of agents that act upon the germination of seeds, fertilizing agents and nutriments. A plant treatment composition can optionally comprise a phyto-acceptable excipient other than a glycerol carbonic ester.

The invention relates also to a method for the treatment of plants, to uses of glycerol carbonic esters as an input in agriculture, to a concentrated colloidal suspension and to a plant treatment composition comprising at least one glycerol carbonic ester, characterized in combination by all or some of the features mentioned hereinabove or hereinbelow.

Other objects, features and advantages of the invention will become apparent upon reading the following description and the implementation examples of the invention, which are given without implying any limitation and in which.

Figure 1:
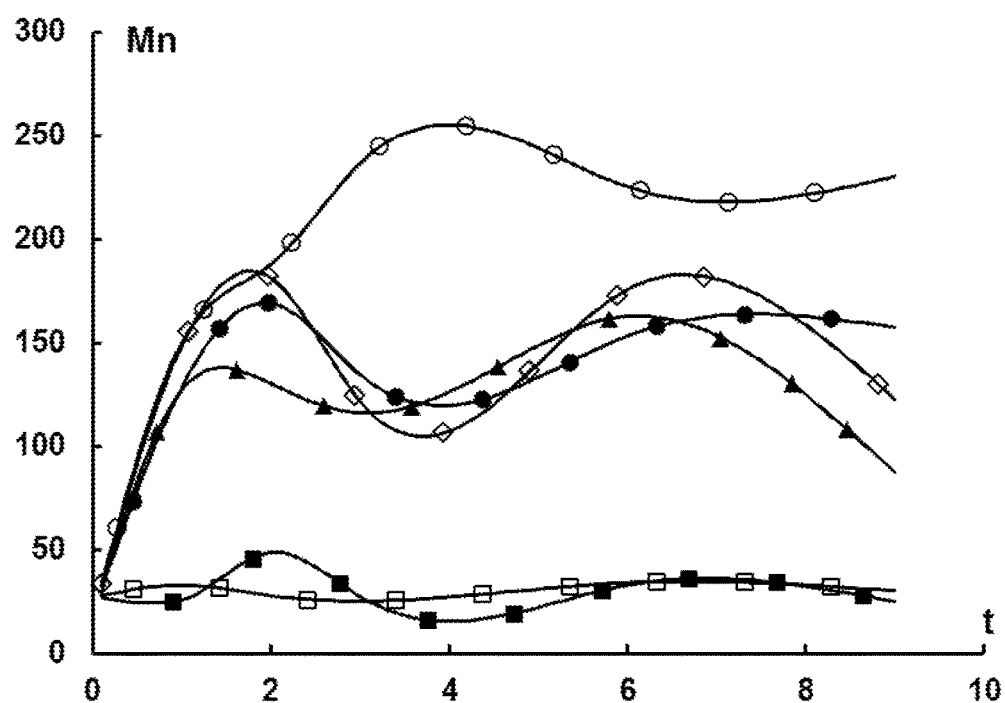
FIG. 1 is a graphic representation of the change in the foliar manganese content of soya plants in cultivation after application of nutritive compositions comprising at least one cyclic glycerol carbonic ester according to the invention and manganese carbonate.

According to the present invention, at least one glycerol carbonic ester, with the exception of the dicyclic glycerol carbonate having 5 ring members, is used as an input in agriculture. It can be a cyclic glycerol carbonic ester or a linear glycerol carbonic ester. A cyclic glycerol carbonic ester can be a glycerol carbonate having a ring with 6 ring members.

The cyclic glycerol carbonate (CAS 931-40-8) having 5 ring members, or 4-(hydroxymethyl)-1,3-dioxolan-2-one, is described, for example, in FR 2 733 232.

The cyclic α/α'-acylated glycerol carbonic esters of the general formula (VIII) can be obtained by any suitable method. In particular, for a use according to the invention, a cyclic α/α'-acylated glycerol carbonic ester of formula (VIII) can be obtained, for example, by a synthesis process in which an acylation of a cyclic glycerol carbonic ester is carried out. For example, such an acylation is carried out by adding cyclic glycerol carbonic ester, dropwise and with stirring, to a liquid medium comprising a quantity of at least one fatty acid (for example, without implying any limitation, heptanoic acid, nonanoic acid, undecylenic acid or oleic acid) and 4-methylbenzenesulfonic acid (CAS no. 6192-52-5, para-toluenesulfonic acid, ApTs) brought to a temperature of approximately 110° C., under a pressure of approximately 800 hPa. The reaction mixture obtained is maintained with stirring at 110° C. and under 900 hPa for approximately 3 hours.

In this manner there are synthesized, for example, the cyclic α/α'-heptanoylated glycerol carbonic ester (ECG-C$_7$), the cyclic α/α'-nonanoylated glycerol carbonic ester (ECG-C$_9$), the cyclic α/α'-undecylenoylated glycerol carbonic ester (ECG-C$_{11:1}$), the cyclic α/α'-oleylated glycerol carbonic ester (ECG-C$_{18:1}$).

It is also possible to obtain such a cyclic α/α'-acylated glycerol carbonic ester of formula (VIII) by adding an anhydride to cyclic glycerol carbonate in the presence of an ion exchange resin.

For example, the cyclic α/α'-acetylated glycerol carbonic ester, or glycerol carbonate acetate (ECG-C$_2$) is obtained by adding acetic anhydride to glycerol in the presence of an ion exchange resin as catalyst and while maintaining the temperature of the reaction medium at 50° C., with mechanical stirring for approximately 4 hours. The glycerol carbonate acetate is purified by the thin film technique at a temperature of 170° C. and under reduced pressure.

Linear α/α'-acylated glycerol carbonic esters and linear β-acylated glycerol carbonic esters can be obtained by a particular process which is derived from the general process described hereinbelow.

Linear α/α'-acylated glycerol carbonic esters—especially oligomers of linear α/α'-acylated glycerol carbonic esters—of the general formula (X) are obtained by synthesis starting from at least one cyclic α/α'-acylated glycerol carbonic ester of the general formula (VIII), at least one organic initiator chosen from the group formed of hydroxylated organic compounds—especially polyols, in particular glycerol—, and at least one metal catalyst chosen, for example, from the group formed of zinc sulfate ($ZnSO_4$), zinc stearate ($Zn(C_{18}H_{35}O_2)_2$), iron sulfate ($FeSO_4$), ferric phosphate ($FePO_4$), manganese sulfate ($MnSO_4$), zinc oxide ($ZnO$), calcium carbonate ($Ca_2CO_3$), sodium carbonate ($Na_2CO_3$) and sodium sulfate ($Na_2SO_4$). In such a synthesis process, the cyclic α/α'-acylated glycerol carbonic esters of formula (VIII), the organic initiator and the metal catalyst are mixed in a reactor which is hermetically sealed and brought to a temperature of from 150° C. to 220° C. and so as to place the liquid mixture under a pressure, named autogenic pressure, which is greater than or equal to atmospheric pressure. In such a synthesis process, the polymerization of the cyclic α/α'-acylated glycerol carbonic esters of the general formula (VIII) and the formation of linear α/α'-acylated glycerol carbonic esters of the general formula (X) are controlled by monitoring the autogenic pressure generated by heating of the hermetically sealed reaction medium.

The mean molar masses of the linear acylated glycerol carbonic esters which are obtainable by the above process are described in Table 1 below.

EXAMPLE 1—Synthesis of Cyclic α/α'-Acylated Glycerol Carbonic Esters

The synthesis of cyclic α/α'-acylated glycerol carbonic esters, in particular of cyclic α/α'-heptanoic glycerol carbonic ester (ECG-C$_7$), cyclic α/α'-nonanoic glycerol carbonic ester (ECG-C$_9$), cyclic α/α'-undecylenoic glycerol carbonic ester (ECG-C$_{11:1}$) and cyclic α/α'-oleic glycerol carbonic ester (ECG-C$_{18:1}$), is carried out by esterification of the cyclic α/α'-hydroxylated glycerol carbonate with a corresponding fatty acid.

1.64 mol of fatty acid and 0.0078 mol of 4-methylbenzenesulfonic acid (CAS no. 6192-52-5, para-toluenesulfonic acid, ApTs) are placed in a 500 ml reactor equipped with a stirring device, a device for placing under reduced pressure and a "Dean-Stark" device for removing the water that forms. The temperature of the mixture is brought to a temperature of 110° C. under reduced pressure of 800 hPa for a period of 15 minutes. 0.84 mol of cyclic α/α'-hydroxylated glycerol carbonate is then added dropwise to the reactor with mechanical stirring at 800 revolutions per minute (rpm) over a period of 15 minutes. The reactor is placed in an oil bath brought to a temperature of 110° C. with mechanical stirring (800 rpm) for 3 hours.

EXAMPLE 2—Purification of Cyclic α/α'-Acylated Glycerol Carbonic Esters

The reaction mixture is diluted in 150 ml of ethyl ether, and the mixture obtained is placed in a 1 liter separating funnel. The mixture is washed in succession with 4 volumes of water saturated with NaCl until the aqueous phase is neutral. The washed organic phase is dried over magnesium sulfate and then separated from the hydrated magnesium sulfate by filtration. The ether of the organic phase is removed by evaporation under reduced pressure. A mass of dry product of 277 g is obtained. The cyclic α/α'-acylated glycerol carbonic ester is separated from the excess fatty acids by thin film distillation under reduced pressure (0.6 hPa) at a temperature that is below the boiling point of the fatty acid under that reduced pressure and below 155° C. The cyclic α/α'-acylated glycerol carbonate is obtained, the purity of which, evaluated by gas phase chromatography, is from 85% to 95%.

EXAMPLE 3—Synthesis of the Cyclic α/α'-Acetylated Glycerol Carbonic Ester (ECG-C$_2$)

472 g of cyclic glycerol carbonate (4-(hydroxymethyl)-1,3-dioxolan-2-one, CAS 931-40-8) and 4 g of Lewatit K2431 resin are placed in a 2-liter three-necked glass flask equipped with a mechanical stirrer and a "Dean-Stark" device for removing the water that forms, containing a coolant and placed in an oil bath. 6 mol of acetic anhydride are added dropwise to the reactor in order to control and maintain the temperature of the reactor at 50° C., with mechanical stirring at 800 rpm for 4 hours.

The excess acetic anhydride is removed by evaporation at a temperature of 60° C. and under reduced pressure of 55 hPa. The linear α/α'-acetylated glycerol carbonic ester is purified by the thin film technique carried out in an evaporator/separator at a temperature of 170° C. and under reduced pressure of 0.33 hPa. The cyclic α/α'-acetylated glycerol carbonic ester is obtained, the purity of which, evaluated by gas phase chromatography, is from 85% to 98%.

The chemical structures of the cyclic α/α'-acylated glycerol carbonic esters synthesized in Examples 1, 2 and 3 are confirmed by mass spectrometry, by proton NMR, by $^{13}$C NMR and by Fourier transform infrared spectroscopy. The purity of the cyclic α/α'-acylated glycerol carbonic esters and the molecular ion mass are given in Table 1 below.

TABLE 1

|  | Purity, % | Mass spectrometry, m/z |
|---|---|---|
| ECG-C$_2$ | 98 | 160.1 |
| ECG-C$_7$ | 94 | 230.2 |
| ECG-C$_9$ | 95 | 258.3 |
| ECG-C$_{11:1}$ | 85 | 284.3 |
| ECG-C$_{18:1}$ | 96 | 382.5 |

EXAMPLE 4—Use of Cyclic Glycerol Carbonate in a Nutritive Composition for the Cultivation of Soya Cyclic glycerol carbonate (CG) of formula (VI), glycerol, water and manganese carbonate (MnCO$_3$) in the form of a solid in the divided state, the solid particles of which have a mean size of approximately 2 μm, are mixed. The proportions by mass are approximately 1.2% cyclic glycerol carbonate, approximately 27.3% glycerol, approximately 10.5% water and approximately 58.7% MnCO$_3$. A concentrated colloidal suspension (CG-Mn500) of MnCO$_3$ which is stable over time and the particles of which do not settle is obtained.

The concentrated colloidal suspension is diluted in water, and the nutritive composition is applied to the crop by fogging (by means of an atomizer) at a rate of 500 grams of manganese carbonate per hectare of crop.

Such a composition permits foliar application of MnCO$_3$ to soya and allows a high foliar manganese carbonate (MnCO$_3$) content of approximately from 110 to 160 ppm to be maintained for a period of approximately from 7 to 8 days. As negative control (Mn500), a suspension of manganese carbonate in water is applied to a cereal crop at a rate of 500 g of manganese carbonate (MnCO$_3$) per hectare of crop. Under the conditions of the negative control, the foliar manganese (Mn) content of the treated soya modality remains low, less than 50 ppm and approximately 30 ppm for 8 days. This foliar MnCO$_3$ content of the negative control is identical to the foliar manganese content obtained by treatment of a cereal crop with a comparable quantity of water ("water").

Figure 2:
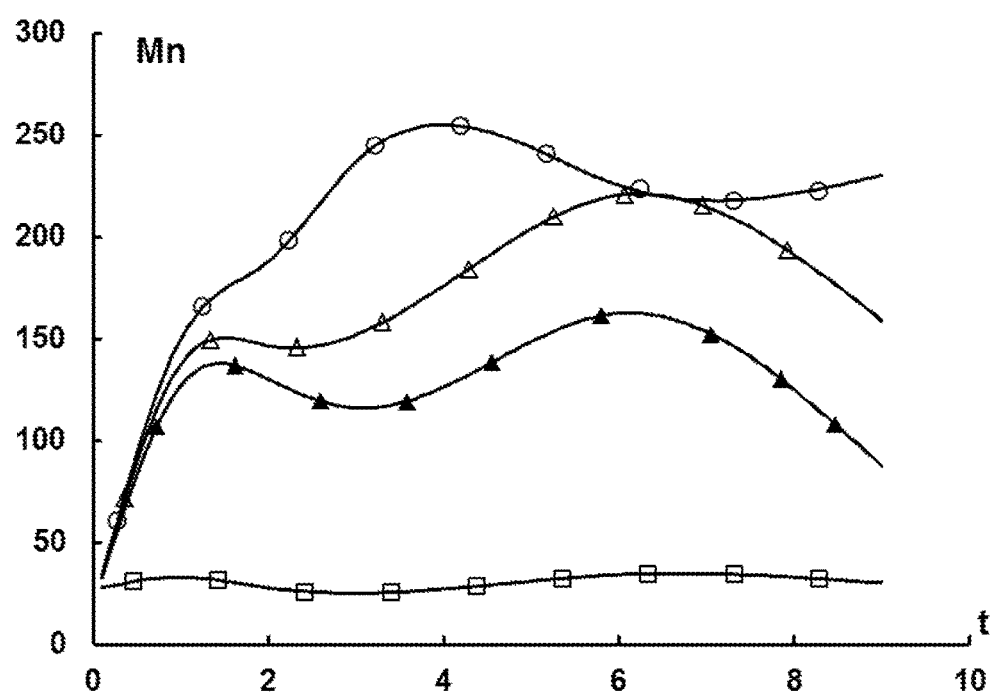
FIG. 2 is a graphic representation of the change in the foliar manganese content of soya plants in cultivation after application of nutritive compositions comprising at least one cyclic α/α'-acylated glycerol carbonic ester according to the invention and manganese carbonate.
Figure 3:
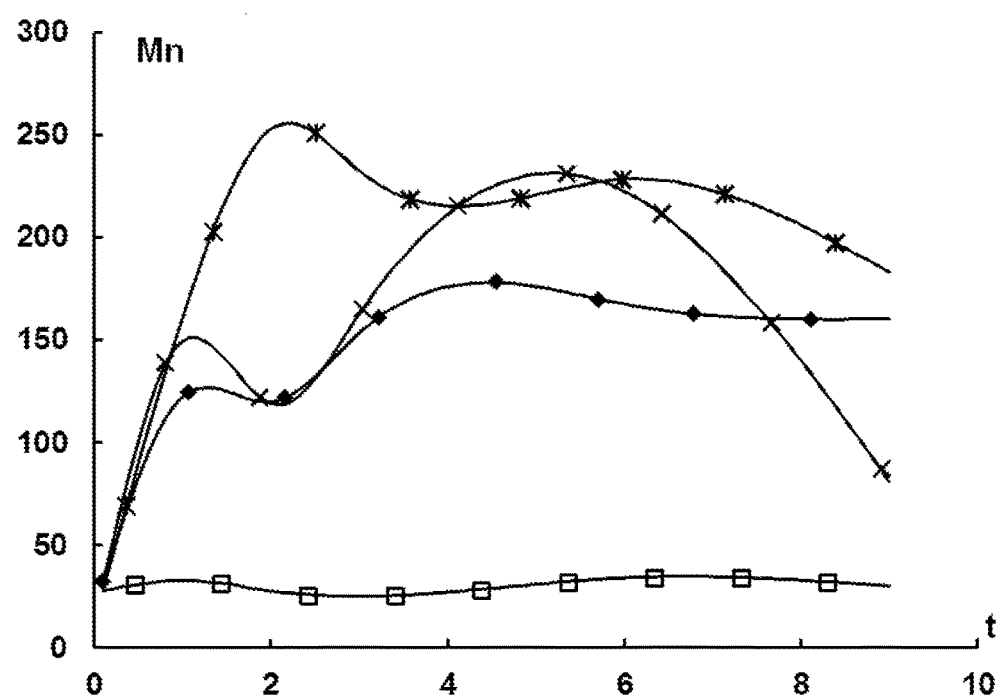
FIG. 3 is a graphic representation of the change in the foliar manganese content of soya plants in cultivation after application of nutritive compositions comprising at least one linear glycerol carbonic ester according to the invention and manganese carbonate.
Figure 4:
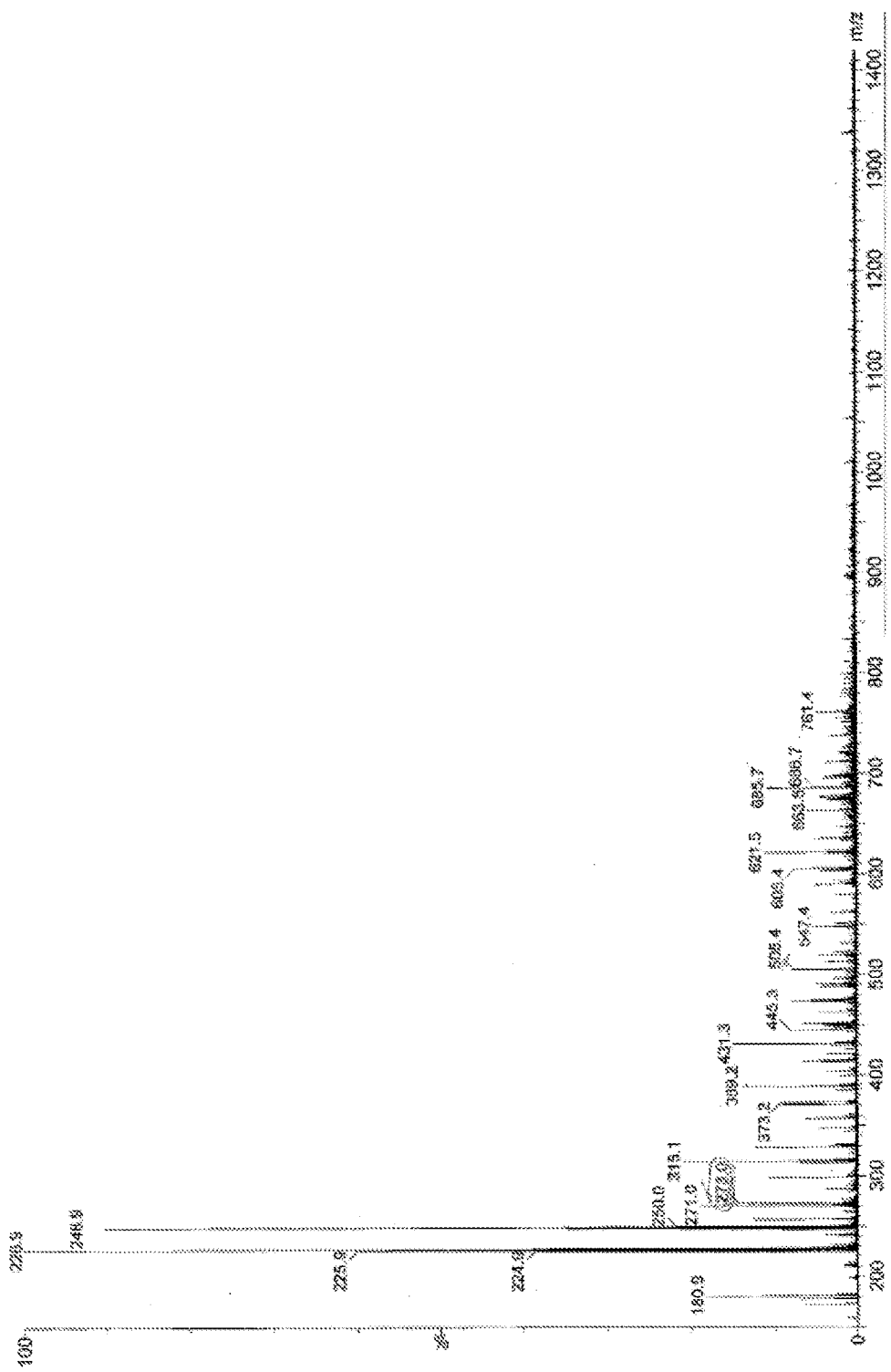
FIG. 4 is a mass spectrum performed on a reaction medium obtained by carrying out a process of oligomerization of the α/α'-acetylated glycerol carbonic ester (ECG-C2) as described in Example 13.

The results are presented in FIGS. 1, 2 and 3, in which:
the control "water" is identified by a solid square (■);
the negative control "Mn500" is identified by an empty square (□);
the cyclic glycerol carbonate "CG Mn500" test is identified by a solid triangle (▲).

EXAMPLE 5—Use of Cyclic Glycerol Carbonate Acetate (ECG-C$_2$) as an Adjuvant in a Nutritive Composition for the Cultivation of Soya Cyclic glycerol carbonate acetate (ECG-C$_2$), glycerol, water and manganese carbonate (MnCO$_3$) in the form of a solid in the divided state, the solid particles of which have a mean size of approximately 2 μm, are mixed. The proportions by mass are approximately 1.25% cyclic glycerol carbonate acetate, approximately 27.3% glycerol, approximately 10.5% water and approximately 58.7% MnCO$_3$. A concentrated colloidal suspension of MnCO$_3$ which is stable over time and the particles of which do not settle is obtained.

The concentrated colloidal suspension is diluted in water, and the nutritive composition is applied to the soya crop by fogging at a rate of 500 grams of manganese carbonate per hectare of crop.

Such a nutritive composition permits foliar application of $MnCO_3$ to soya and allows a high foliar manganese carbonate ($MnCO_3$) content of approximately from 100 to 180 ppm to be maintained for a period greater than 8 days. The results are presented in FIG. 1 ($ECG-C_2$ is identified by an empty diamond (◇)).

EXAMPLE 6—Use of Cyclic Glycerol Carbonate as an Adjuvant in a Nutritive Composition Cyclic glycerol carbonate of formula (VI), glycerol, water, manganese carbonate ($MnCO_3$) and manganese sulfate ($MnSO_4$), $MnCO_3$ and $MnSO_4$ being in the form of solids in the divided state, the solid particles of which have a mean size of approximately 2 µm, are mixed. The proportions by mass are approximately 1.2% cyclic glycerol carbonate acetate, approximately 1.97% glycerol, approximately 25.6% water, approximately 55.2% $MnCO_3$ and approximately 12.1% $MnSO_4$. A concentrated colloidal suspension of $MnCO_3$ and $MnSO_4$ which is stable over time and the particles of which do not settle is obtained.

This suspension can be diluted to obtain a nutritive composition, or it can be added to a nutritive composition formulation, especially for the cultivation of soya.

EXAMPLE 7—Use of Cyclic Glycerol Carbonate as an Adjuvant in a Nutritive Composition Cyclic glycerol carbonate of formula (VI), glycerol, water and manganese carbonate ($MnCO_3$) in the form of a solid in the divided state, the solid particles of which have a mean size of approximately 2 µm, are mixed. The proportions by mass are approximately 1.22% cyclic glycerol carbonate acetate, approximately 8.15% glycerol, approximately 20.38% water and approximately 67.61% $MnCO_3$. A concentrated colloidal suspension of $MnCO_3$ which is stable over time and the particles of which do not settle is obtained.

This suspension can be diluted to obtain a nutritive composition, or it can be added to a nutritive composition formulation, especially for the cultivation of soya.

EXAMPLE 8—Use of Cyclic Glycerol Carbonate Acetate ($ECG-C_2$) as an Adjuvant in a Nutritive Composition for the Cultivation of Soya Cyclic glycerol carbonate acetate ($ECG-C_2$), oleic triglycerides (THO), an oleic acid salt, glycerol, water and manganese carbonate ($MnCO_3$) in the form of a solid in the divided state, the solid particles of which have a mean size of approximately 2 µm, are mixed. The proportions by mass are approximately 1.5% cyclic glycerol carbonate acetate, approximately 39.5% glycerol, approximately 7.5% water, approximately 1% oleic triglyceride, approximately 0.5% oleate and approximately 50% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to a soya crop by fogging at a rate of 500 grams of manganese carbonate per hectare of crop.

Such a nutritive composition permits foliar application of $MnCO_3$ to soya and allows a high foliar manganese carbonate content of from 150 to 220 ppm to be maintained for a period greater than 8 days. The results are presented in FIG. 2 (THO/$ECG-C_2$ is identified by an empty triangle (△)).

EXAMPLE 9—Use of Cyclic Glycerol Carbonate Heptanoate ($ECG-C_7$) as an Adjuvant in a Nutritive Composition for the Cultivation of Soya Cyclic glycerol carbonate heptanoate ($ECG-C_7$), glycerol, water and manganese carbonate ($MnCO_3$) in the form of a solid in the divided state, the solid particles of which have a mean size of approximately 2 µm, are mixed. The proportions by mass are approximately 1.23% cyclic glycerol carbonate heptanoate, approximately 24.6% glycerol, approximately 14.4% water and approximately 57.5% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya, does not cause burning on the soya leaves and allows a high foliar manganese content to be maintained.

EXAMPLE 10—Use of Cyclic Glycerol Carbonate Nonanoate ($ECG-C_9$) as an Adjuvant in a Nutritive Composition for the Cultivation of Soya Cyclic glycerol carbonate nonanoate ($ECG-C_9$), glycerol, water and manganese carbonate ($MnCO_3$) in the form of a solid in the divided state, the solid particles of which have a mean size of approximately 2 µm, are mixed. The proportions by mass are approximately 1.23% cyclic glycerol carbonate nonanoate, approximately 24.6% glycerol, approximately 14.4% water and approximately 57.5% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya, does not cause burning on the soya leaves, and allows a high foliar manganese content to be maintained.

EXAMPLE 11—Use of Cyclic Glycerol Carbonate Undecylenate ($ECG-C_{11:1}$) as an Adjuvant in a Nutritive Composition for the Cultivation of Soya Cyclic glycerol carbonate undecylenate ($ECG-C_{11:1}$), glycerol, water and manganese carbonate ($MnCO_3$) in the form of a solid in the divided state, the solid particles of which have a mean size of approximately 2 µm, are mixed. The proportions by mass are approximately 1.23% cyclic glycerol carbonate undecylenate, approximately 24.65% glycerol, approximately 14.4% water and approximately 57.5% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya and allows a high foliar manganese ($MnCO_3$) content of from 120 to 160 ppm to be maintained for a period greater than 8 days. The results are presented in FIG. 1 (ECG-$C_{11:1}$ is identified by a solid circle (●)).

EXAMPLE 12—Use of Cyclic Glycerol Carbonate Oleate (ECG-$C_{18:1}$) as an Adjuvant in a Nutritive Composition for the Cultivation of Soya Cyclic glycerol carbonate oleate (ECG-$C_{18:1}$), glycerol, water and manganese carbonate ($MnCO_3$) in the form of a solid in the divided state, the solid particles of which have a mean size of approximately 2 μm, are mixed. The proportions by mass are approximately 1.23% cyclic glycerol carbonate oleate, approximately 24.65% glycerol, approximately 14.4% water and approximately 57.5% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to a soya crop by fogging at a rate of 500 grams of manganese carbonate per hectare of crop.

Such a nutritive composition permits foliar application of $MnCO_3$ to a soya crop, an increase in the foliar manganese content until four days after its application to reach a maximum foliar manganese content of greater than 250 ppm, and maintenance of a foliar manganese content of from 200 to 250 ppm for a period of greater than 8 days. The results are presented in FIG. 1 (ECG-$C_{11:1}$ is identified by an empty circle (○)).

EXAMPLE 13—Synthesis of Acetylated Glycerol Oligomers (OECG-$C_2$) by Oligomerization of the Cyclic α/α'-Acetylated Glycerol Carbonic Ester (ECG-$C_2$)

21.25 g of ECG-$C_2$ as obtained in Example 3, 125 mg of zinc stearate ($Zn(C_{18}H_{35}O_2)_2$) as catalyst and 3.75 g of glycerol are brought into contact in a reactor, which is hermetically sealed. The reaction mixture is then heated in the hermetically sealed reactor to reach a temperature of 160° C. under autogenous pressure, and then the pressure is returned to atmospheric pressure and the temperature of 160° C. is maintained for 2 hours at atmospheric pressure. The rate of conversion of ECG-$C_2$ is 98%. Analysis by gel-permeation chromatography shows the formation of oligomers of number-average molecular mass 714 g/mol, 335 g/mol, 206 g/mol, 139 g/mol and 92 g/mol.

An example of a mass spectrum performed on a reaction medium obtained by carrying out a process of oligomerization of the α/α-acetylated glycerol carbonic ester (ECG-$C_2$) as described in Example 13 is shown in FIG. 4. There are detected signals corresponding to molecular ions and fragments of m/z values of from 180.9 to 761.4 and corresponding to oligomers of the following formulae (A), (B) and (C):

(A)

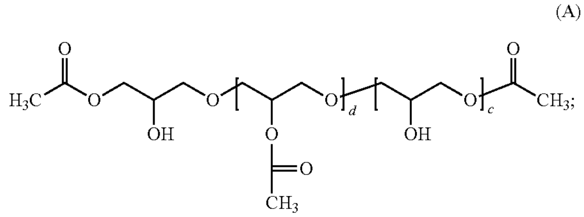

wherein c can have the value 1, 2 or 4 and d can have the value 1, 2, 3 or 4;

(B)

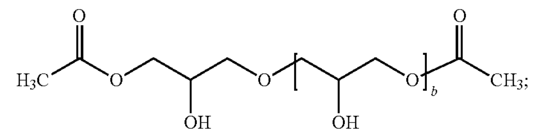

wherein b can have the value 1, 2 or 3;

(C)

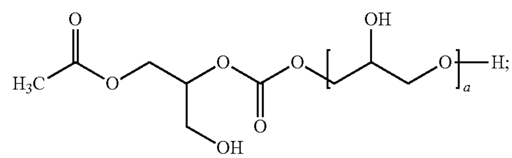

wherein a is 1, 2, 3, 4, 5, 6, 7 or 8; and (D)

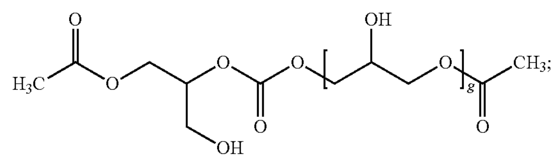

wherein g can have the value 1, 2, 3, 4, 5, 6, 7, 8, 9 or 10.

EXAMPLE 14—Synthesis of Acetylated Glycerol Oligomers (OECG-$C_2$) by Oligomerization of the Cyclic α/α'-Acetylated Glycerol Carbonic Ester (ECG-$C_2$)

21.25 g of ECG-$C_2$ as obtained in Example 3, 125 mg of zinc sulfate ($ZnSO_4$) as catalyst and 3.75 g of glycerol as organic initiator are brought into contact in a reactor, which is hermetically sealed. The reaction mixture is then heated in the hermetically sealed reactor to reach a temperature of 160° C. under autogenous pressure, and then the pressure is returned to atmospheric pressure and the temperature of 160° C. is maintained for 2 hours at atmospheric pressure. The rate of conversion of ECG-$C_2$ is 66%. Analysis by gel-permeation chromatography shows the formation of oligomers of number-average molecular mass 389 g/mol, 159 g/mol and 83 g/mol.

EXAMPLE 15—Use of a Composition Comprising Acetylated Glycerol Oligomers (OECG-$C_2$) as an Adjuvant in a Nutritive Composition for the Cultivation of Soya A composition comprising oligomers (OECG-$C_2$) as described in Example 13, glycerol, water and manganese carbonate ($MnCO_3$) in the form of a solid in the divided state, the solid particles of which have a mean size of approximately 2 μm, are mixed. The proportions by mass in the mixture are approximately 1.25% OECG-$C_2$, approximately 27.72% glycerol, approximately 10.41% water and approximately 58.33% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya, does not cause burning on the soya leaves and allows a high foliar manganese content to be maintained for at least 8 days. The results are presented in FIG. 3 (OECG-$C_2$ treatment is identified by a solid diamond (♦)).

EXAMPLE 16—Use of a Composition Comprising Glycerol Oligomers (OECG-$C_2$) as an Adjuvant in a Nutritive Composition for the Cultivation of Soya A composition comprising oligomers (OECG-$C_2$) as described in Example 13, cyclic glycerol carbonate acetate (ECG-$C_2$) as described in Example 3, glycerol, water and manganese carbonate ($MnCO_3$) in the form of a solid in the divided state, the solid particles of which have a mean size of approximately 2 μm, are mixed. The proportions by mass are approximately 1.25% OECG-$C_2$, approximately 0.2% ECG-$C_2$, approximately 27.72% glycerol, approximately 10.41% water and approximately 58.33% $MnCO_3$. A concentrated colloidal suspension of $MnCO_3$ which is stable over time and the $MnCO_3$ particles of which do not settle is obtained. Such a concentrated colloidal suspension further comprises zinc stearate.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya, an increase in the foliar manganese content from the first day following application and up to four days after application, reaching a foliar manganese content of approximately 180 ppm, and the maintenance of a foliar manganese content of greater than 150 ppm for a period greater than 8 days.

EXAMPLE 17—Use of a Composition Comprising Glycerol Oligomers (OECG-$C_2$) as an Adjuvant in a Nutritive Composition for the Cultivation of Soya A composition comprising oligomers (OECG-$C_2$) as described in Example 14, cyclic glycerol carbonate acetate (ECG-$C_2$) as described in Example 3, glycerol, water and manganese carbonate ($MnCO_3$) in the form of a solid in the divided state, the solid particles of which have a mean size of approximately 2 μm, are mixed. The proportions by mass are approximately 1.25% OECG-$C_2$, approximately 0.55% ECG-$C_2$, approximately 27.72% glycerol, approximately 10.41% water and approximately 58.33% $MnCO_3$. A concentrated colloidal suspension of $MnCO_3$ which is stable over time and the $MnCO_3$ particles of which do not settle is obtained. Such a concentrated colloidal suspension further comprises zinc stearate.

The concentrated colloidal suspension is diluted in water, and the diluted nutritive composition is applied to the soya crop by fogging at a rate of 500 grams of manganese carbonate per hectare of crop.

Such a nutritive composition permits foliar application of $MnCO_3$ to soya, an increase in the foliar manganese content from the first day following application and up to four days after application, reaching a foliar manganese content of approximately 180 ppm, and the maintenance of a foliar manganese content of greater than 150 ppm for a period greater than 8 days.

EXAMPLE 18—Synthesis of Heptanoylated Glycerol Oligomers (OECG-$C_7$) by Oligomerization of the Cyclic α/α'-Heptanoylated Glycerol Carbonic Ester (ECG-$C_7$)

20 g of ECG-$C_7$ as obtained in Examples 1 and 2, 113 mg of zinc sulfate ($ZnSO_4$) as catalyst and 2.42 g of glycerol as organic initiator are brought into contact in a reactor, which is hermetically sealed. The reaction mixture is then heated in the hermetically sealed reactor to reach a temperature of 200° C. under autogenous pressure, and then the pressure is returned to atmospheric pressure and the temperature of 200° C. is maintained for 2 hours at atmospheric pressure. The rate of conversion of ECG-$C_7$ is 64%. Analysis by gel-permeation chromatography shows the formation of oligomers of number-average molecular mass 639 g/mol, 420 g/mol, 252 g/mol and 96 g/mol.

EXAMPLE 19—Use of a Nutritive Composition Comprising Oligomers of Linear Glycerol Carbonate (OECG-$C_7$) for the Cultivation of Soya A composition comprising oligomers (OECG-$C_7$) as described in Example 18, glycerol, water and manganese carbonate ($MnCO_3$) in the form of a solid in the divided state, the solid particles of which have a mean size of approximately 2 μm, are mixed. The proportions by mass are approximately 0.625% OECG-$C_7$, approximately 22.915% glycerol, approximately 15.84% water and approximately 58.33% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by spraying at a rate of 500 grams of manganese carbonate per hectare of crop. This nutritive composition permits foliar application of $MnCO_3$ to soya and does not cause burning on the soya leaves.

EXAMPLE 20—Synthesis of Nonanoylated Glycerol Oligomers (OECG-$C_9$) by Oligomerization of the Cyclic α/α'-Nonanoylated Glycerol Carbonic Ester (ECG-$C_9$)

20 g of ECG-$C_9$ as obtained in Examples 1 and 2, 110 mg of zinc sulfate ($ZnSO_4$) as catalyst and 2.15 g of glycerol as organic initiator are brought into contact in a reactor, which is hermetically sealed. The reaction mixture is then heated in the hermetically sealed reactor to reach a temperature of 180° C. under autogenous pressure, and then the pressure is returned to atmospheric pressure and the temperature of 180° C. is maintained for 2 hours at atmospheric pressure. The rate of conversion of ECG-$C_9$ is 88%. Analysis by gel-permeation chromatography shows the formation of oligomers of number-average molecular mass 992 g/mol, 541 g/mol, 303 g/mol and 90 g/mol.

EXAMPLE 21—Use of a Nutritive Composition Comprising Glycerol Oligomers (OECG-$C_9$) for the Cultivation of Soya A composition comprising oligomers (OECG-$C_9$) as described in Example 20, glycerol, water and manganese carbonate ($MnCO_3$) in the form of a solid in the divided state, the solid particles of which have a mean size of approximately 2 μm, are mixed. The proportions by mass are approximately 0.625% OECG-$C_9$, approximately 22.915% glycerol, approximately 15.84% water and approximately 58.33% $MnCO_3$. A concentrated colloidal suspension of $MnCO_3$ which is stable over time and the $MnCO_3$ particles of which do not settle is obtained. The concentrated colloidal suspension is diluted in water, and the diluted nutritive composition is applied to the soya crop by spraying at a rate of 500 grams of manganese carbonate per hectare of crop. This nutritive composition permits foliar application of $MnCO_3$ to soya without causing burning.

EXAMPLE 22—Synthesis of Undecylenoylated Glycerol Oligomers (OECG-$C_{11:1}$) by Oligomerization of the Cyclic α/α'-Undecylenoylated Glycerol Carbonic Ester (ECG-$C_{11:1}$)

10 g of ECG-$C_{11:1}$ as obtained in Examples 1 and 2, 86 mg of zinc sulfate ($ZnSO_4$) as catalyst and 1.3 g of glycerol as organic initiator are brought into contact in a reactor, which is hermetically sealed. The reaction mixture is then heated in the hermetically sealed reactor to reach a temperature of 190° C. under autogenous pressure, and then the pressure is returned to atmospheric pressure and the temperature of 190° C. is maintained for 2 hours at atmospheric pressure. The rate of conversion of ECG-$C_{11:1}$ is 98%. Analysis by gel-permeation chromatography shows the formation of oligomers of number-average molecular mass 7632 g/mol, 2113 g/mol, 1084 g/mol, 750 g/mol and 486 g/mol.

EXAMPLE 23—Use of a Nutritive Composition Comprising Glycerol Oligomers (OECG-$C_{11:1}$) for the Cultivation of Soya A composition comprising oligomers (OECG-$C_{11:1}$) as described in Example 22, glycerol, water and manganese carbonate ($MnCO_3$) in the form of a solid in the divided state, the solid particles of which have a mean size of approximately 2 μm, are mixed. The proportions by mass are approximately 0.625% OECG-$C_{11:1}$, approximately 22.915% glycerol, approximately 15.84% water and approximately 58.33% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by spraying at a rate of 500 grams of manganese carbonate per hectare of crop. Such a nutritive composition does not cause burning on the soya leaves.

Such a nutritive composition permits an increase in the foliar $MnCO_3$ content from the first day following application and up to four days after application, reaching a foliar manganese content of approximately 260 ppm two days after application, and the maintenance of a foliar manganese content of greater than 200 ppm for a period of 8 days. The results are presented in FIG. 3 (OECG-$C_{11:1}$) is identified by a star (*)).

EXAMPLE 24—Synthesis of α/α'-Oleylated Glycerol Oligomers (OECG-$C_{18:1}$) by Oligomerization of the Cyclic α/α'-Oleylated Glycerol Carbonic Ester (ECG-$C_{18:1}$)

10 g of ECG-$C_{18:1}$ as obtained in Examples 1 and 2, 50 mg of zinc sulfate ($ZnSO_4$) as catalyst and 0.7 g of glycerol as organic initiator are brought into contact in a reactor, which is hermetically sealed. The reaction mixture is then heated in the hermetically sealed reactor to reach a temperature of 200° C. under autogenous pressure, and then the pressure is returned to atmospheric pressure and the temperature of 200° C. is maintained for 2 hours at atmospheric pressure. The rate of conversion of ECG-$C_{18:1}$ is 97%. Analysis by gel-permeation chromatography shows the formation of oligomers of number-average molecular mass 3724 g/mol, 1787 g/mol, 1169 g/mol, 613 g/mol and 94 g/mol.

EXAMPLE 25—Use of a Nutritive Composition Comprising Glycerol Oligomers (OECG-$C_{18:1}$) for the Cultivation of Soya A composition comprising oligomers (OECG-$C_{18:1}$) as described in Example 24, glycerol, water and manganese carbonate ($MnCO_3$) in the form of a solid in the divided state, the solid particles of which have a mean size of approximately 2 μm, are mixed. The proportions by mass are approximately 0.625% OECG-$C_{18:1}$, approximately 22.915% glycerol, approximately 15.84% water and approximately 58.33% $MnCO_3$. A concentrated colloidal suspension of $MnCO_3$ which is stable over time and the $MnCO_3$ particles of which do not settle is obtained.

The concentrated colloidal suspension is diluted in water, and the diluted nutritive composition is applied to the soya crop by spraying at a rate of 500 grams of manganese carbonate per hectare of crop. This nutritive composition does not cause burning on the soya leaves.

Such a nutritive composition permits an increase in the foliar manganese content from the first day following application, then an increase in the foliar manganese content up to four days after application, reaching a maximum value of 230 ppm, and a decline in the foliar manganese content to a value of less than 100 ppm eight days after application. The results are presented in FIG. 3 (OECG-$C_{18:1}$ is identified by a cross (x)). Such a nutritive composition therefore permits delayed release of the manganese.

EXAMPLE 26—Comparative Test of an Adjuvant According to the Invention with the Composition MANTRAC 500 on Foliar $MnCO_3$ Absorption A powder of manganese carbonate ($MnCO_3$, CAS 598-62-9) having a mean particle size of substantially approximately 2 μm is prepared by grinding. A concentrated colloidal suspension comprising 58.7% of this powder in a liquid composition comprising 1.5% glycerol carbonate acetate (ECG-$C_2$, as described in Example 3 and in Table 1), 39.5% glycerol, 7.5% water and 1% jojoba oil, the indicated percentages being percentages by mass. The concentrated colloidal suspension is diluted in water to form a treatment composition (Mn385) according to the invention which is suitable for applying, by spraying on the cultivated surface area, a quantity of manganese carbonate of 385 g per hectare of cultivated surface area.

There are also prepared:

- a concentrated colloidal suspension as described in Example 4, and this concentrated colloidal suspension is diluted in water to form a nutritive composition (Mn457) according to the invention which is suitable for applying, by spraying, a quantity of manganese carbonate of 457 g per hectare of surface area; and
- a concentrated colloidal suspension as described in Example 7, and this concentrated colloidal suspension is diluted in water to form a nutritive composition (Mn509) according to the invention which is suitable for applying, by spraying, a quantity of manganese carbonate of 509 g per hectare of cultivated surface area.

The nutritive compositions Mn385, Mn457 and Mn509 according to the invention are applied by spraying to plots of 4 parcels having a surface area of 16 m² cultivated with winter common wheat (variety "Quality", ARVALIS).

There are also prepared in parallel:
on a plot of 4 16 m² parcels, a crop of winter common wheat treated by spraying with water, as negative control; and
on a plot of 4 16 m² parcels, a crop of winter common wheat treated with $MnCO_3$ on its own (without adjuvant according to the invention) at a rate of 500 g per hectare, as control treatment; and
on a plot of 4 16 m² parcels, a crop of winter common wheat treated, by way of comparison, with a formulation of MANTRAC 500 at a rate of 500 g of $MnCO_3$ per hectare.

The results obtained in the case of the control treatment with $MnCO_3$ on its own (without adjuvant according to the invention) do not differ from the results obtained with the negative control.

The manganese content retained in the leaves of treated common wheat is measured one day (D+1), seven days (D+7), 14 days (D+14) and 21 days (D+21) after application. To that end, the leaves are removed and washed three times with water to remove the manganese carbonate that has not been absorbed by the plant, and the manganese absorbed into the leaves is then assayed. The results are given in Table 2 below and are expressed in ppm (μg of manganese per gram of leaf).

treated cereals to be increased as compared with those same cereals in cultivation treated with a composition not in accordance with the invention (MANTRAC 500) comprising the same quantity of manganese (500 g/l), in particular 1 day after the treatment, 7 days after the treatment and 21 days after the treatment.

EXAMPLE 27—Effect of the Foliar Application of a Nutritive $MnCO_3$ Composition According to the Invention on the Nutrition of the Wheat with Macroelements ($N_{total}$, $C_{total}$, P, K, Ca, Mg) and with Microelements (Fe, Cu, Zn, B)

A concentrated colloidal suspension comprising 58.7% manganese carbonate powder (having a mean particle size of substantially approximately 2 μm) is prepared in a liquid composition comprising 1.5% glycerol carbonate acetate ($ECG-C_2$, as described in Example 3 and in Table 1), 39.5% glycerol, 7.5% water and 1% jojoba oil as described in Example 26. This concentrated colloidal suspension is diluted in water to form a nutritive composition according to the invention, which is applied to a wheat crop.

Statistical analysis, named principal component analysis, of the kinetic measurement of the foliar manganese, macroelement and microelement contents 1 day (D+1), 7 days (D+7), 14 days (D+14) and 21 days (D+21) after application of the nutritive manganese composition makes it possible to show the effect of the nutritive composition according to the invention on the overall nutrition of the plant. Table 3 below gives the values of the correlation coefficients of the foliar manganese content relative to the values of the foliar contents of the various macroelements and microelements. Values close to 1 reflect a synergy in the improvement in the overall nutrition of the plant when the manganese deficiency

TABLE 2

|  | D + 1 | D + 7 | D + 14 | D + 21 |
|---|---|---|---|---|
| $MnCO_3$ on its own | 84.83 +/− 28.01 | 74.83 +/− 19.14 | 112.50 +/− 45.35 | 95.43 +/− 5.95 |
| MANTRAC 500 | 228.07 +/− 139.40 | 171.75 +/− 13.38 | 157.55 +/− 60.81 | 188.00 +/− 38.16 |
| Mn385 | 192.00 +/− 58.92 | 138.75 +/− 20.71 | 164.25 +/− 27.18 | 153.00 +/− 39.61 |
| Mn457 | 211.00 +/− 49.79 | 163.25 +/− 44.66 | 177.25 +/− 41.02 | 177.00 +/− 18.25 |
| Mn509 | 329.00 +/− 55.87 | 204.25 +/− 44.62 | 180.75 +/− 67.31 | 210.33 +/− 29.50 |

It is observed that the application of Mn509 allows the foliar Mn content to be increased relative to MANTRAC 500 at D+1, D+7, D+14 and D+21.

Mn509 treatment allows a foliar $MnCO_3$ content to be obtained that is greater than the foliar $MnCO_3$ content obtained in the case of treatment with MANTRAC 500.

The use of $ECG-C_2$ further allows a foliar $MnCO_3$ content to be obtained that is substantially equivalent to the foliar $MnCO_3$ content obtained with MANTRAC 500 but with an application of $MnCO_3$ (Mn457) at a rate of 457 g of $MnCO_3$ per hectare.

The kinetics of daily $MnCO_3$ assimilation in the leaves are measured. For the composition Mn509, a daily assimilation of manganese which increases starting from the day of treatment and continues until at least 21 days after application is observed. By comparison, the daily assimilation by the common wheat treated with the composition Mn509 is twice the daily assimilation by the common wheat treated with the composition MANTRAC 500.

Treatment of a cereal in cultivation with the nutritive $MnCO_3$ composition according to the invention by foliar application therefore allows the foliar manganese content of in the wheat is removed. The negative values reflect an antagonistic effect of removing the manganese deficiency on the nutrition.

TABLE 3

| Variables | D + 1 Mn | D + 7 Mn | D + 14 Mn | D + 21 Mn |
|---|---|---|---|---|
| $N_{total}$, % | −0.497 | −0.538 | 0.704 | 0.611 |
| $C_{total}$, % | −0.559 | 0.429 | 0.914 | −0.185 |
| P, % | 0.690 | 0.849 | −0.205 | 0.887 |
| K, % | −0.660 | 0.377 | −0.804 | −0.886 |
| Ca, % | 0.918 | 0.936 | 0.072 | 0.928 |
| Mg, % | 0.774 | 0.919 | −0.071 | 0.948 |
| Fe, % | 0.366 | −0.796 | 0.047 | −0.139 |
| Cu, % | 0.171 | 0.573 | 0.195 | 0.261 |
| Zn, % | 0.801 | 0.989 | −0.145 | −0.451 |
| B, % | 0.330 | 0.070 | 0.009 | −0.326 |

Nutritive treatment of a cereal in cultivation with a nutritive composition comprising $MnCO_3$ by foliar application permits balancing of the nutritional status and harmonization of the nutrition with the macroelements calcium, magnesium and phosphorus and with the microelement zinc within a period of from one day to 21 days after application and of the nitrogen nutrition starting from the second week after application (D+14).

EXAMPLE 28—Foliar Application of an $MnCO_3$ Suspension According to the Invention on the Nitrogen Nutrition of Wheat The change in the foliar nitrogen content in the days following treatment of parcels of wheat treated by foliar application of a negative control (CNNT) and of the treatment compositions MANTRAC500, Mn385, Mn457 and Mn509 of Example 26 is analyzed. The negative control (CNNT) shows a continuous reduction in the foliar nitrogen content. This reduction corresponds to nitrogen remobilization during leafing of the plant, in particular during the phase of grain filling. MANTRAC500 treatment brings about an increase in the nitrogen content in the leaves up to 7 days after treatment, then a reduction in foliar nitrogen owing to nitrogen mobilization into the grains. Mn385 treatment allows the foliar nitrogen content to be maintained for 13 days after treatment, followed by a reduction in foliar nitrogen. Mn457 treatment causes an increase in the nitrogen content in the leaves up to 11 days after treatment, followed by a reduction in foliar nitrogen. Mn509 treatment allows the foliar nitrogen content to be maintained for 11 days after treatment by delaying the phase of foliar nitrogen remobilization.

EXAMPLE 29—Nutritive Efficiency of a Manganese Carbonate Suspension According to the Invention on a Manganese-Deficient Soya Crop

TABLE 4

| | |
|---|---|
| 7 September | Sowing of soybeans on moist perlite |
| 20 September | Transplantation of the soya plants on Valmarque sand washed with hydrochloric acid |
| 22 September | Supply of a nutritive Mn composition at 10% of the specified dos |
| 29 September | Supply of a nutritive solution without Mn |
| 6 October | Renewal of the nutritive solution without Mn |
| 13 October | Renewal of the nutritive solution without Mn |
| 20 October | Renewal of the nutritive solution without Mn |
| 27 October | Renewal of the nutritive solution without Mn |
| 2 November | 1st harvest for analysis at $D_0$ and foliar treatment |
| 3 November | Renewal of the nutritive solution without Mn 2nd harvest for analysis at $D_1$ |
| 4 November | 3rd harvest for analysis at $D_2$ |
| 5 November | 4th harvest for analysis at $D_3$ |
| 8 November | 5th harvest for analysis at $D_6$ |
| 9 November | Renewal of the nutritive solution without Mn |
| 11 November | 6th harvest for analysis at $D_9$ |

Soya plants (variety Amphor) that are deficient in manganese are chosen.

Each of the chosen parcels receives a treatment by fogging with one of the treatment compositions $T_1$, $T_2$, $T_3$, $T_4$, $T_5$ and $T_6$ described in Table 5 below. Each manganese-deficient soya crop parcel is treated with 100 ml of pulp ($T_1$, $T_2$, $T_3$, $T_4$, $T_5$ and $T_6$) comprising 4 g of manganese ($MnSO_4$ and/or $MnCO_3$) corresponding to a treatment dose of 500 g/ha of manganese.

TABLE 5

| Treatment composition | Manganese applied (in g/ha) | Treatment composition | ml of stock solution in 100 ml |
|---|---|---|---|
| $T_1$ | | Water | 0 |
| $T_2$ | 400 ($MnCO_3$) | Example 26 | 10 |
| $T_3$ | 500 ($MnCO_3$) | Example 4 | 8 |
| $T_4$ | 500 ($MnCO_3$) 80 ($MnSO_4$) | Example 6 | 6, 9 |
| $T_5$ | 600 ($MnCO_3$) | Example 7 | 6, 7 |
| $T_6$ | 500 ($MnCO_3$) | Example 15 | 8 |

For each analysis of the foliar manganese content at $D_0$, $D_1$, $D_2$, $D_3$, $D_6$ and $D_9$, the soya leaves removed are washed once with a 2% solution of acetic acid in demineralized water and then twice with demineralized water. The leaves are then dried for 48 hours at a temperature of 75° C. Three analyses are carried out in parallel.

The nutritive compositions $T_2$, $T_3$, $T_4$, $T_5$ and $T_6$ permit rapid manganese assimilation from application of the treatment and for one to two days following application of the treatment. Application of composition $T_2$ (ECG-$C_2$ and jojoba oil, $MnCO_3$ at 400 g/ha) shows sustained and increasing manganese assimilation, which increases from 130 ppm to 160 ppm between the second and the ninth day following the treatment.

Compositions $T_3$, $T_4$ and $T_5$ (ECG-$C_2$) show a strong and temporary initial (first and second days) assimilation, followed by renewed assimilation around the seventh and eighth day following the treatment.

Composition $T_6$ (OECG-$C_2$) shows moderate and temporary initial (first day) assimilation, but a renewal of assimilation which is at a maximum at four days and is sustained until the ninth day after the treatment.

The choice of the glycerol carbonic esters and the quantity of solid in the divided state applied to the plants allow the assimilation profile of the solid in the divided state in the plants to be modulated.

EXAMPLE 30—Treatment of Barley Seeds

The seeds of a plant chosen, for example, from the group formed of maize, barley, rape and a forage plant such as Raygrass are treated. To that end, barley seeds (variety Orjoie, RAGT) having a weight of 17.1 g per 300 grains are chosen. The seeds are coated/film-coated with a composition comprising oligomers (OECG-$C_2$) as described in Example 14 at a rate of a maximum quantity of 1 liter of oligomer composition per tonne of seeds. The seeds and the oligomer composition are mixed, and the mixture is left to dry.

The germinating power of the barley seeds treated with the composition comprising oligomers (OECG-$C_2$) at a rate of 0.1, 0.25, 0.5 and 1 liter/tonne of seeds is analyzed, and the value of the germinating power obtained under each of those conditions is compared with the value of the germinating power of "control" seeds treated with the same quantity of water. The germinating power, expressed as the percentage of grains that have germinated after five days, obtained with treatments of 0.1 liter/tonne, 0.25 liter/tonne, 0.5 liter/tonne (90.1%) and 1 liter/tonne is greater by 3.6% to 7.3% than the value of the germinating power of the "control" (82.8%).

EXAMPLE 31—Treatment of Maize Seeds

Maize seeds (PR33V15, Pioneer) having a weight of 60.7 g per 200 grains are chosen. The seeds are coated/film-coated with a composition comprising oligomers (OECG-$C_2$) as described in Example 14 at a rate of a maximum quantity of 1 liter of oligomer composition per tonne of seeds. The seeds and the oligomer composition are mixed, and the mixture is left to dry.

The germinating power of the maize seeds treated with the composition comprising oligomers (OECG-$C_2$) at a rate of 0.1, 0.25 and 0.5 liter/tonne of seeds is analyzed, and the value of the germinating power obtained under each of those conditions is compared with the value of the germinating power of "control" seeds treated with the same quantity of water. The germinating power, expressed as the percentage of grains that have germinated after five days, obtained with treatments of 0.1 liter/tonne, 0.25 liter/tonne and 0.5 liter/tonne (90.1%) is greater by 1.3% to 1.6% than the value of the germinating power of the "control".

EXAMPLE 32—Analysis of the Vegetative Development of the Parts of Plants Above the Soil and of the Root Parts of Plants Grown from Seeds Maize and barley seeds previously treated by coating/film-coating with a composition comprising oligomers (OECG-$C_2$) as described in Examples 30 and 31 are cultivated on sand. After 15 days' growth, the parts above the soil (leaves) and the root parts of the plantlets are separated and weighed. Treatments with 0.1 liter/tonne and 0.25 liter/tonne lead to an increase of 29% and 11%, respectively, in the total mass (parts above the soil and root parts) of the plantlets and of 40% and 23% of the mass of the root parts relative to the "control" plantlets.

EXAMPLE 33—Synergistic Effect of a Composition According to the Invention Comprising Oligomers (OECG-$C_2$) and a Mineral Nutritional Supplement Maize seeds are coated/film-coated as described in Example 31 with a composition comprising manganese (SeedFlow Mn) at a rate of 3 liters/tonne of seeds and the composition comprising oligomers (OECG-$C_2$) at a rate of 0.25 liter/tonne of seeds. An increase in the germinating power of the seeds treated with manganese and the composition of oligomers (OECG-$C_2$) of 3% relative to the germinating power of seeds treated with the manganese composition or with the composition of oligomers is observed.

EXAMPLE 34—Synergistic Effect of a Composition According to the Invention Comprising Oligomers (OECG-$C_2$) and a Endomycorrhizal Fungus Barley seeds are coated/film-coated as described in Example 30 with the composition comprising oligomers (OECG-$C_2$) and an endomycorrhizal fungus. An increase in the germinating power of the seeds treated with the endomycorrhizal fungus relative to "control" seeds and an increase of approximately 2% in the germinating power of the seeds treated with the endomycorrhizal fungus and with the composition comprising oligomers (OECG-$C_2$) relative to the germinating power of the seeds treated with an endomycorrhizal fungus alone is observed.

EXAMPLE 35—Stimulation of Photosynthesis

A nutritive composition (Mn/OECG-$C_{11:1}$) comprising oligomers (OECG-$C_{11:1}$) and manganese carbonate as described in Examples 22 and 23 is applied to soya plants by spraying, at a rate of 500 grams of manganese carbonate per hectare of crop. Immediately after application of the nutritive composition, the chlorophyll fluorescence is measured on leaves of soya plants that have received the nutritive composition and, by way of control, on leaves of soya plants that have not received the nutritive composition.

An increased photosynthetic efficiency value (0.836) is observed for the treatment with the nutritive composition (Mn/OECG-$C_{11:1}$), as compared with the photosynthetic efficiency value (0.831) of the control not treated with the oligomer.

EXAMPLE 36—Stimulation of Photosynthesis

A nutritive composition (Mn/OECG-$C_{18:1}$) comprising oligomers (OECG-$C_{18:1}$) and manganese carbonate as described in Examples 24 and 25 is applied to soya plants by spraying, at a rate of 500 grams of manganese carbonate per hectare of crop. Immediately after application of the nutritive composition, the chlorophyll fluorescence is measured on leaves of soya plants that have received the nutritive composition and, by way of control, on leaves of soya plants that have not received the nutritive composition.

An increased photosynthetic efficiency value (0.848) is observed for the treatment with the nutritive composition (Mn/OECG-$C_{18:1}$), as compared with the photosynthetic efficiency value (0.831) of the control not treated with the oligomer.

It goes without saying that the invention can be the subject of numerous variant embodiments and applications. Of course, this description and these examples are given only by way of illustrative examples, and the person skilled in the art will be able to provide numerous modifications, variations and applications thereof without departing from the scope of the invention.

The invention claimed is:
1. A method for the treatment of plants, comprising:
applying to a plant at least one glycerol carbonic ester, with the exception of a cyclic glycerol carbonate having five ring members, the glycerol carbonic ester being selected from the group consisting of:
(i) linear glycerol carbonic esters having at least one group of atoms of general formula (I):

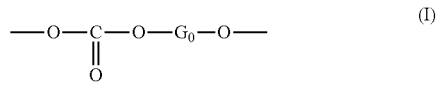

wherein
$G_0$ is selected from the group consisting of:
α/α'-acylated propylene groups of general formula (II):

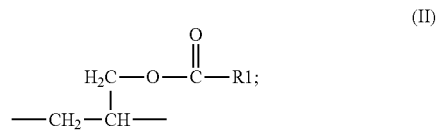

β-acylated propylene groups of general formula (III):

(III)

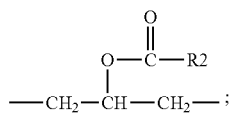

the α/α'-hydroxylated propylene group of formula (IV):

(IV)

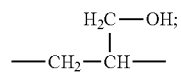

the β-hydroxylated propylene group of formula (V):

(V)

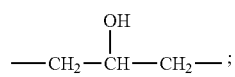

wherein R1 and R2 are organic groups formed of elements selected from the group consisting of carbon (C), hydrogen (H) and oxygen (O); and (ii) cyclic α/α'-acylated glycerol carbonic esters of general formula (VIII):

(VIII)

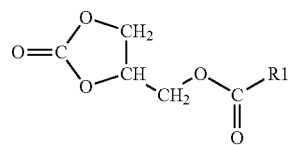

wherein R1 is an organic group formed of elements selected from the group consisting of carbon (C), hydrogen (H) and oxygen (O);

wherein the at least one glycerol carbonic ester is applied by contacting a part of the plant elected from the group consisting of a plant seed, a part of the plant above soil, an underground part of the plant, and combinations thereof.

2. The method of claim 1, wherein the at least one glycerol carbonic ester is a linear acylated glycerol carbonic ester of general formula (X):

(X)

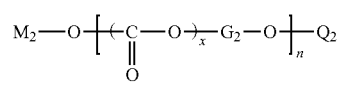

wherein:

x is an integer equal to 0 or to 1 which can vary in formula (X) according to each group of formula (X-a):

(X-a)

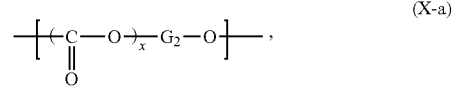

x not always being zero;

n is an integer from 1 to 20 inclusive;

$Q_2$ is a hydrogen (H) or an organic group formed of at least two atoms bonded by covalent bonds, said atoms being selected from the group consisting of carbon (C), hydrogen (H) and oxygen (O);

$M_2$ represents an organic group formed of at least two atoms bonded by covalent bonds, said atoms being selected from the group consisting of carbon (C), hydrogen (H) and oxygen (O); and $G_2$ represents:

α/α'-acylated propyl group of the general formula (II); or

β-acylated propyl group of the general formula (III).

3. The method of claim 2, wherein n is an integer from 1 to 10.

4. The method of claim 2, wherein the linear α/α'-acylated glycerol carbonic ester of the general formula (X) has a molar mass greater than 400 g/mol.

5. The method of claim 1, wherein R1 and R2 are aliphatic hydrocarbon groups having from 1 to 25 carbon atoms.

6. The method of claim 1, wherein the at least one glycerol carbonic ester is applied in association with at least one active agent, other than a glycerol carbonic ester, selected from the group consisting of agents that act upon the germination of seeds, growth control agents, plant development agents, agents that stimulate photosynthesis, and nutriments for plants.

7. The method of claim 1, wherein the at least one glycerol carbonic ester is applied by contacting the plant with a nutritive composition comprising at least one glycerol carbonic ester and at least one solid in the divided state comprising at least one compound selected from the group consisting of nutritive elements of plants.

8. The method of claim 1, wherein the at least one glycerol carbonic ester is applied to plant seeds.

9. The method of claim 1, wherein the at least one glycerol carbonic ester is applied to parts of plants above the soil.

10. The method of claim 1, wherein the at least one glycerol carbonic ester is applied to underground parts of plants.

* * * * *